United States Patent [19]
Chambers et al.

[11] Patent Number: 5,849,746
[45] Date of Patent: Dec. 15, 1998

[54] SUBSTITUTED 1,4-PIPERAZINE-HETEROARYL DERIVATIVES AS 5-HT$_{1D}$ RECEPTOR AGONISTS

[75] Inventors: Mark Stuart Chambers, Puckeridge; Angus Murray MacLeod, Bishops Stortford, both of Great Britain; Victor Giulio Matassa, Rome, Italy

[73] Assignee: Merck Sharp & Dohme Ltd., Hoddesdon, England

[21] Appl. No.: 894,302

[22] PCT Filed: Jan. 29, 1996

[86] PCT No.: PCT/GB96/00179

§ 371 Date: Jul. 22, 1997

§ 102(e) Date: Jul. 22, 1997

[87] PCT Pub. No.: WO96/23785

PCT Pub. Date: Aug. 8, 1996

[30] Foreign Application Priority Data

Jan. 31, 1995 [GB] United Kingdom .................. 9501865

[51] Int. Cl.⁶ .................. A61K 31/495; C07D 403/14; C07D 413/14
[52] U.S. Cl. .................. 514/253; 544/366; 544/367; 544/368; 544/369; 544/370; 544/371; 544/373; 544/372
[58] Field of Search .................. 544/366, 367, 544/369, 370, 371, 373, 372; 514/253

[56] References Cited

U.S. PATENT DOCUMENTS

| | | | |
|---|---|---|---|
| 5,455,351 | 10/1995 | Kempf et al. ............... | 544/366 |
| 5,552,402 | 9/1996 | Matassa et al. ............. | 544/366 |
| 5,614,524 | 3/1997 | Matassa et al. ............. | 514/253 |
| 5,618,816 | 4/1997 | Crenshaw et al. ........... | 514/253 |

FOREIGN PATENT DOCUMENTS

| | | |
|---|---|---|
| 0 438 230 A2 | 7/1991 | European Pat. Off. . |
| 0 464 558 A1 | 1/1992 | European Pat. Off. . |
| 0 464 604 A2 | 1/1992 | European Pat. Off. . |
| 0 494 774 A1 | 7/1992 | European Pat. Off. . |
| 0 497 512 A2 | 8/1992 | European Pat. Off. . |
| 0 511 610 A1 | 11/1992 | European Pat. Off. . |
| 0 548 813 A1 | 6/1993 | European Pat. Off. . |
| 0 648 767 A1 | 4/1995 | European Pat. Off. . |
| WO 91/18897 | 12/1991 | WIPO . |
| WO 92/13856 | 8/1992 | WIPO . |
| WO 93/18029 | 9/1993 | WIPO . |
| WO 94/02477 | 2/1994 | WIPO . |
| WO 95/32196 | 11/1995 | WIPO . |

*Primary Examiner*—Emily Bernhardt
*Attorney, Agent, or Firm*—Philippe L. Durette; Melvin Winokur

[57] ABSTRACT

A class of 1,4-disubstituted piperazine derivatives, further substituted on one of the carbon atoms of the piperazine ring, are selective agonists of 5-HT$_1$-like receptors, being potent agonists of the human 5-HT$_{1D\alpha}$ receptor subtype whilst possessing at least a 10-fold selective affinity for the 5-HT$_{1D\alpha}$ receptor subtype relative to the 5-HT$_{1D\beta}$ subtype; they are therefore useful in the treatment and/or prevention of clinical conditions, in particular migraine and associated disorders, for which a subtype-selective agonist of 5-HT$_{1D}$ receptors is indicated, while eliciting fewer side-effects, notably adverse cardiovascular events, than those associated with non-subtype-selective 5-HT$_{1D}$ receptor agonists.

7 Claims, No Drawings

SUBSTITUTED 1,4-PIPERAZINE-HETEROARYL DERIVATIVES AS 5-HT$_{1D}$ RECEPTOR AGONISTS

The present invention relates to a class of substituted piperazine derivatives which act on 5-hydroxytryptamine (5-HT) receptors, being selective agonists of so-called "5-HT$_1$-like" receptors. They are therefore useful in the treatment of clinical conditions for which a selective agonist of these receptors is indicated.

It has been known for some time that 5-HT$_1$-like receptor agonists which exhibit selective vasoconstrictor activity are of use in the treatment of migraine (see, for example, A. Doenicke et al., *The Lancet,* 1988, Vol. 1, 1309–11; and W. Feniuk and P. P. A. Humphrey, *Drug Development Research,* 1992, 26, 235–240).

The human 5-HT$_1$-like or 5-HT$_{1D}$ receptor has recently been shown by molecular cloning techniques to exist in two distinct subtypes. These subtypes have been termed 5-HT$_{1D\alpha}$ (or 5-HT$_{1D-1}$) and 5-HT$_{1D\beta}$ (or 5-HT$_{1D-2}$), and their amino acid sequences are disclosed and claimed in WO-A-91/17174.

The 5-HT$_{1D\alpha}$ receptor subtype in humans is believed to reside on sensory terminals in the dura mater. Stimulation of the 5-HT$_{1D\alpha}$ subtype inhibits the release of inflammatory neuropeptides which are thought to contribute to the headache pain of migraine. The human 5-HT$_{1D\beta}$ receptor subtype, meanwhile, is located predominantly on the blood vessels and in the brain, and hence may play a part in mediating constriction of cerebral and coronary arteries, as well as CNS effects.

Administration of the prototypical 5-HT$_{1D}$ agonist sumatriptan (GR43175) to humans is known to give rise at therapeutic doses to certain adverse cardiovascular events (see, for example, F. Willett et al., *Br. Med. J.,* 1992, 304, 1415; J. P. Ottervanger et al., The Lancet, 1993, 341, 861–2; and D. N. Bateman, *The Lancet,* 1993, 341, 221–4). Since sumatriptan barely discriminates between the human 5-HT$_{1D\alpha}$ and 5-HT$_{1D\beta}$ receptor subtypes (cf. WO-A-91/17174, Table 1), and since it is the blood vessels with which the 5-HT$_{1D\beta}$ subtype is most closely associated, it is believed that the cardiovascular side-effects observed with sumatriptan can be attributed to stimulation of the 5-HT$_{1D\beta}$ receptor subtype. It is accordingly considered (cf. G. W. Rebeck et al., *Proc. Natl. Acad. Sci. USA,* 1994, 91, 3666–9) that compounds which can interact selectively with the 5-HT$_{1D\alpha}$ receptor subtype, whilst having a less pronounced action at the 5-HT$_{1D\beta}$ subtype, might be free from, or at any rate less prone to, the undesirable cardiovascular and other side-effects associated with non-subtype-selective 5-HT$_{1D}$ receptor agonists, whilst at the same time maintaining a beneficial level of anti-migraine activity.

The compounds of the present invention, being selective 5-HT$_1$-like receptor agonists, are accordingly of benefit in the treatment of migraine and associated conditions, e.g. cluster headache, chronic paroxysmal hemicrania, headache associated with vascular disorders, tension headache and paediatric migraine. In particular, the compounds according to this invention are potent agonists of the human 5-HT$_{1D\alpha}$ receptor subtype. Moreover, the compounds in accordance with this invention have been found to possess at least a 10-fold selective affinity for the 5-HT$_{1D\alpha}$ receptor subtype relative to the 5-HT$_{1D\beta}$ subtype, and they can therefore be expected to manifest fewer side-effects than those associated with non-subtype-selective 5-HT$_{1D}$ receptor agonists.

Several distinct classes of substituted five-membered heteroaromatic compounds are described in published European patent applications 0438230, 0494774 and 0497512, and published International patent applications 93/18029, 94/02477 and 94/03446. The compounds described therein are stated to be agonists of 5-HT$_1$-like receptors, and accordingly to be of particular use in the treatment of migraine and associated conditions. None of these publications, however, discloses nor even suggests the substituted piperazine derivatives provided by the present invention.

In EP-A-0548813 is described a series of alkoxypyridin-4-yl and alkoxypyrimidin-4-yl derivatives of indol-3-ylalkylpiperazines which are alleged to provide treatment of vascular or vascular-related headaches, including migraine. There is, however, no disclosure nor any suggestion in EP-A-0548813 of replacing the alkoxypyridine or alkoxypyrimidine substituent with any other substituent; nor of substituting on the carbon atoms of the piperazine nucleus with anything other than lower alkyl; nor indeed is there any suggestion therein that the range of substituents specified at the 5-position of the indole moiety might be successfully replaced by an optionally substituted five-membered heteroaromatic ring.

Moreover, nowhere in the prior art mentioned above is there any disclosure of a subtype-selective 5-HT$_{1D}$ receptor agonist having a 5-HT$_{1D\alpha}$ receptor binding affinity (IC$_{50}$) below 50 nM and at least a 10-fold selective affinity for the 5-HT$_{1D\alpha}$ receptor subtype relative to the 5-HT$_{1D\beta}$ subtype.

WO-A-95/32196, published on 30 Nov. 1995, describes a class of substituted piperazine, piperidine and tetrahydropyridine derivatives as alpha subtype-selective agonists of the 5-HT$_{1D}$ receptor. However, there is no disclosure nor any suggestion therein of piperazine derivatives possessing a substituent on one of the carbon atoms of the piperazine nucleus.

The compounds according to the present invention are subtype-selective 5-HT$_{1D}$ receptor agonists having a human 5-HT$_{1D\alpha}$ receptor binding affinity (IC$_{50}$) below 50 nM, typically below 10 nM and preferably below 1 nM; and at least a 10-fold selective affinity, typically at least a 50-fold selective affinity and preferably at least a 100-fold selective affinity, for the human 5-HT$_{1D\beta}$ receptor subtype relative to the 5-HT$_{1D\beta}$ subtype.

The present invention provides a compound of formula I, or a salt or prodrug thereof:

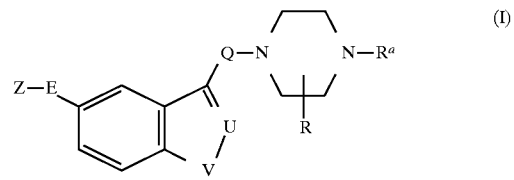

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole;

E represents a chemical bond or a straight or branched alkylene chain containing from 1 to 4 carbon atoms;

Q represents a straight or branched alkylene chain containing from 1 to 6 carbon atoms, optionally substituted in any position by a hydroxy group;

U represents nitrogen or C—R$^2$;

V represents oxygen, sulphur or N—R$^3$;

R represents a group of formula —W—R$^1$;

W represents a carbonyl group (C=O), or a straight or branched alkylene chain containing from 1 to 4 carbon atoms;

R1 represents —OR$^x$, —OCOR$^x$, —OCONR$^x$R$^y$, —NR$^x$R$^y$, —NR$^z$COR$^x$ or —NR$^z$CONR$^x$R$^y$;

R$^x$ and R$^y$ independently represent hydrogen, hydrocarbon or a heterocyclic group, or R$^x$ and R$^y$ together represent a C$_{2-6}$ alkylene group;

R$^a$ and R$^z$ independently represent hydrogen, hydrocarbon or a heterocyclic group; and R$^2$ and R$^3$ independently represent hydrogen or C$_{1-6}$ alkyl.

The present invention also provides a compound of formula I as defined above, or a salt or prodrug thereof, in which W represents a straight or branched alkylene chain containing from 1 to 4 carbon atoms.

The five-membered heteroaromatic ring Z in the compounds of formula I above may be optionally substituted by one or, where possible, two substituents. As will be appreciated, where Z represents an oxadiazole, thiadiazole or tetrazole ring, only one substituent will be possible; otherwise, one or two optional substituents may be accommodated around the five-membered heteroaromatic ring Z. Examples of suitable substituents on the five-membered heteroaromatic ring Z include C$_{1-6}$ alkyl, C$_{2-6}$ alkenyl, C$_{2-6}$ alkynyl, C$_{3-7}$ cycloalkyl, aryl, aryl(C$_{1-6}$)alkyl, C$_{3-7}$ heterocycloalkyl, heteroaryl, heteroaryl(C$_{1-6}$)alkyl, C$_{1-6}$ alkoxy, C$_{1-6}$ alkylthio, amino, C$_{1-6}$ alkylamino, di(C$_{1-6}$)alkylamino, halogen, cyano or trifluoromethyl.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include C$_{1-6}$ alkyl, C$_{2-6}$ alkenyl, C$_{2-6}$ alkynyl, C$_{3-7}$ cycloalkyl, C$_{3-7}$ cycloalkyl(C$_{1-6}$)alkyl, aryl and aryl(C$_{1-6}$) alkyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include C$_{3-7}$ heterocycloalkyl, C$_{3-7}$ heterocycloalkyl(C$_{1-6}$)alkyl, heteroaryl and heteroaryl(C$_{1-6}$)alkyl groups.

Suitable alkyl groups include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups include straight-chained and branched alkenyl groups containing from 2 to 6 carbon atoms. Typical examples include vinyl and allyl groups.

Suitable alkynyl groups include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups include phenyl and naphthyl.

Particular aryl(C$_{1-6}$)alkyl groups include benzyl, phenethyl, phenylpropyl and naphthylmethyl.

Suitable heterocycloalkyl groups include azetidinyl, pyrrolidinyl, piperidinyl, piperazinyl and morpholinyl groups.

Suitable heteroaryl groups include pyridyl, quinolyl, isoquinolyl, pyridazinyl, pyrimidinyl, pyrazinyl, pyranyl, furyl, benzofuryl, dibenzofuryl, thienyl, benzthienyl, pyrrolyl, indolyl, pyrazolyl, indazolyl, oxazolyl, isoxazolyl, thiazolyl, isothiazolyl, imidazolyl, benzimidazolyl, oxadiazolyl, thiadiazolyl, triazolyl and tetrazolyl groups.

The expression "heteroaryl(C$_{1-6}$)alkyl" as used herein includes furylmethyl, furylethyl, thienylmethyl, thienylethyl, oxazolylmethyl, oxazolylethyl, thiazolylmethyl, thiazolylethyl, imidazolylmethyl, imidazolylethyl, oxadiazolylmethyl, oxadiazolylethyl, thiadiazolylmethyl, thiadiazolylethyl, triazolylmethyl, triazolylethyl, tetrazolylmethyl, tetrazolylethyl, pyridylmethyl, pyridylethyl, pyrimidinylmethyl, pyrazinylmethyl, quinolylmethyl and isoquinolylmethyl.

The hydrocarbon and heterocyclic groups may in turn be optionally substituted by one or more groups selected from C$_{1-6}$ alkyl, adamantyl, phenyl, halogen, C$_{1-6}$ haloalkyl, C$_{1-6}$ aminoalkyl, trifluoromethyl, hydroxy, C$_{1-6}$ alkoxy, aryloxy, keto, C$_{1-3}$ alkylenedioxy, nitro, cyano, carboxy, C$_{2-6}$ alkoxycarbonyl, C$_{2-6}$ alkoxycarbonyl(C$_{1-6}$)alkyl, C$_{2-6}$ alkylcarbonyloxy, arylcarbonyloxy, C$_{2-6}$ alkylcarbonyl, arylcarbonyl, C$_{1-6}$ alkylthio, C$_{1-6}$ alkylsulphinyl, C$_{1-6}$ alkylsulphonyl, arylsulphonyl, —NR$^v$R$^w$, —NR$^v$COR$^w$, —NR$^v$CO$_2$R$^w$, —NR$^v$SO$_2$R$^w$, —CH$_2$NR$^v$SO$_2$R$^w$, —NHCONR$^v$R$^w$, —CONR$^v$R$^w$, —SO$_2$NR$^v$R$^w$ and —CH$_2$SO$_2$NR$^v$R$^w$, in which R$^v$ and R$^w$ independently represent hydrogen, C$_{1-6}$ alkyl, aryl or aryl(C$_{1-6}$)alkyl, or R$^v$ and R$^w$ together represent a C$_{2-6}$ alkylene group.

When R$^x$ and R$^y$, or R$^v$ and R$^w$, together represent a C$_{2-6}$ alkylene group, this group may be an ethylene, propylene, butylene, pentamethylene or hexamethylene group, preferably butylene or pentamethylene.

The term "halogen" as used herein includes fluorine, chlorine, bromine and iodine, especially fluorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in Design of Prodrugs, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

The optionally substituted five-membered heteroaromatic ring Z in formula I is suitably a 1,3-oxazole, 1,3-thiazole, imidazole, 1,2,4-oxadiazole, 1,3,4-oxadiazole, 1,2,4-thiadiazole, 1,3,4-thiadiazole, 1,2,3-triazole, 1,2,4-triazole or tetrazole ring. Preferably, the ring is a 1,3-oxazole, 1,3-thiazole, 1,2,4-oxadiazole, 1,2,4-thiadiazole or 1,2,4-triazole ring, in particular a 1,2,4-triazol-1-yl or 1,2,4-triazol-4-yl moiety.

Suitably, the five-membered heteroaromatic ring Z is unsubstituted. Examples of optional substituents which may typically be attached to the moiety Z include methyl, ethyl, benzyl and amino.

Where E, Q and W, which may be the same or different, represent straight or branched alkylene chains, these may be, for example, methylene, ethylene, 1-methylethylene, propylene, 2-methylpropylene or butylene. In addition, the alkylene chain Q may be substituted in any position by a hydroxy group giving rise, for example, to a 2-hydroxypropylene or 2-hydroxymethyl-propylene chain Q. Moreover, E may represent a chemical bond such that the moiety Z is attached directly to the benzo moiety of the central fused bicyclic heteroaromatic ring system.

Suitably, E represents a chemical bond or a methylene linkage.

Suitably, Q represents a propylene linkage.

The compound of formula I in accordance with the present invention is suitably an indole, benzofuran or benzthiophene derivative of formula IA, or an indazole derivative of formula IB:

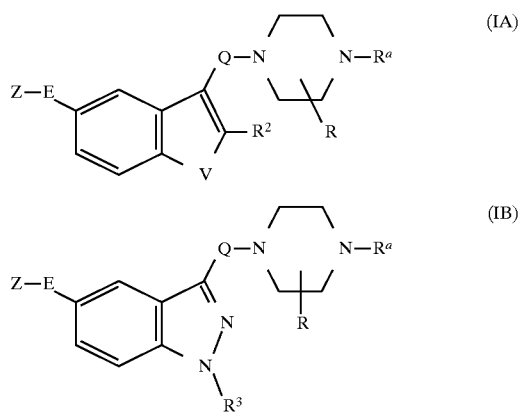

wherein Z, E, Q, V, R, $R^a$, $R^2$ and $R^3$ are as defined above. Preferably, the compounds according to the invention are indole derivatives of formula IC:

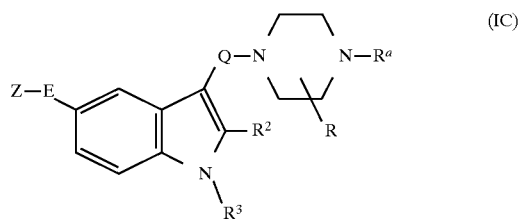

wherein Z, E, Q, R, $R^a$, $R^2$ and $R^3$ are as defined above, in particular wherein $R^2$ and $R^3$ are both hydrogen.

Suitably, W represents a carbonyl group or a methylene linkage. More particularly, W represents a methylene linkage.

Suitably, $R^x$ and $R^y$ independently represent hydrogen, $C_{1-6}$ aryl, aryl($C_{1-6}$)alkyl, heteroaryl or heteroaryl($C_{1-6}$) alkyl, any of which groups may be optionally substituted by one or more substituents selected typically from hydroxy, $C_{1-6}$ alkoxy, amino, $C_{2-6}$ alkylcarbonylamino, $C_{1-6}$ alkylsulphonylamino and $C_{1-6}$ alkylaminosulphonylmethyl.

Particular values of $R^x$ and $R^y$ include hydrogen, methyl, benzyl, methoxy-benzyl, acetylamino-benzyl, 1-phenylethyl, 2-phenylethyl, 2-hydroxy-1-phenylethyl, 1-(acetylamino-phenyl)ethyl, 2-(acetylaminophenyl)ethyl, 1-hydroxy-3-phenylprop-2-yl, 1-hydroxy-1-phenylprop-2-yl, furylmethyl, thienylmethyl and pyridylmethyl. More particularly, $R^x$ and $R^y$ may independently represent hydrogen, methyl or benzyl.

Suitable values for the substituent $R^1$ include hydroxy, benzyloxy, methoxy-benzyloxy, pyridylmethoxy, amino, methylamino, benzylamino, N-(acetylamino-benzyl)-amino, N-(1-phenylethyl)-amino, N-(2-phenylethyl)-amino, N-(2-hydroxy-1-phenylethyl)-amino, N-[1-(acetylaminophenyl)ethyl]-amino, N-[2-(acetylamino-phenyl)ethyl]-amino, N-(1-hydroxy-3-phenylprop-2-yl)-amino, N-(1-hydroxy-1-phenylprop-2-yl)-amino, N-(furylmethyl)-amino, N-(pyridylmethyl)-amino, dimethylamino, N-benzyl-N-methylamino, N-(acetylamino-benzyl)-N-methylamino, N-(2-hydroxy-1-phenylethyl)-N-methylamino, N-[2-(acetylamino-phenyl)ethyl]-N-methylamino, N-methyl-N-(thienylmethyl)-amino and acetylamino. Particular values of $R^1$ include hydroxy, benzylamino, dimethylamino, N-benzyl-N-methylamino and acetylamino.

Particular values of the group R include hydroxymethyl, benzyloxymethyl, benzylaminomethyl, N-(acetylamino-benzyl)-aminomethyl, N-(1-phenylethyl)-aminomethyl, N-(2-hydroxy-1-phenylethyl)-aminomethyl, N-[1-(acetylamino-phenyl)ethyl]-aminomethyl, N-(furylmethyl)-aminomethyl, N-(pyridylmethyl)-aminomethyl, dimethylaminomethyl, N-benzyl-N-methyl-aminomethyl, N-(acetylaminobenzyl)-N-methyl-aminomethyl, N-benzyl-N-methylaminocarbonyl and acetylaminomethyl. More particularly, R may represent hydroxymethyl, benzylaminomethyl, dimethylaminomethyl, N-benzyl-N-methylaminocarbonyl or acetylaminomethyl.

Suitable values of $R^a$ and $R^z$ include hydrogen, methyl and benzyl. Suitably, $R^a$ is hydrogen, methyl or benzyl. Suitably, $R^z$ is hydrogen.

Suitably, $R^2$ and $R^3$ independently represent hydrogen or methyl, especially hydrogen.

A particular sub-class of compounds according to the invention is represented by the compounds of formula II, and salts and prodrugs thereof:

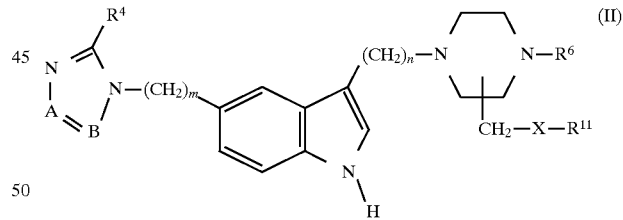

wherein
m is zero, 1, 2 or 3, preferably zero or 1;
n is 2, 3 or 4, preferably 3;
A represents nitrogen or CH;
B represents nitrogen or C—$R^5$;
X represents oxygen or N—$R^{12}$;
$R^4$ and $R^5$ independently represent hydrogen, $C_{1-6}$ alkyl, $C_{2-6}$ alkenyl, $C_{3-7}$ cycloalkyl, aryl, aryl($C_{1-6}$)alkyl, $C_{3-7}$ heterocycloalkyl, heteroaryl, heteroaryl($C_{1-6}$)alkyl, $C_{1-6}$ alkoxy, $C_{1-6}$ alkylthio, amino, $C_{1-6}$ alkylamino, di($C_{1-6}$)alkylamino, halogen, cyano or trifluoromethyl;
$R^6$ represents hydrogen, $C_{1-6}$ alkyl, aryl($C_{1-6}$)alkyl or heteroaryl($C_{1-6}$)alkyl; and
$R^{11}$ and $R^{12}$ independently represent hydrogen, $C_{1-6}$ alkyl, $C_{2-6}$ alkylcarbonyl, aryl, aryl($C_{1-6}$)alkyl, heteroaryl or heteroaryl($C_{1-6}$)alkyl, any of which groups may be optionally substituted.

Examples of suitable optional substituents on the groups $R^{11}$ and $R^{12}$ include halogen, cyano, trifluoromethyl, hydroxy, $C_{1-6}$ alkoxy, $C_{2-6}$ alkylcarbonyl, amino, $C_{1-6}$ alkylamino, di($C_{1-6}$)alkylamino, $C_{2-6}$ alkylcarbonylamino, $C_{1-6}$ alkylsulphonylamino and $C_{1-6}$ alkylaminosulphonylmethyl.

Particular values of $R^4$ and $R^5$ include hydrogen, methyl, ethyl, benzyl and amino, especially hydrogen.

Particular values of $R^6$ include hydrogen, methyl, benzyl and pyridylmethyl, especially methyl or benzyl.

In one embodiment of the compounds of formula II above, $R^6$ represents hydrogen, aryl($C_{1-6}$)alkyl or heteroaryl ($C_{1-6}$)alkyl.

Particular values of $R^{11}$ and $R^{12}$ include hydrogen, methyl, acetyl, benzyl, methoxy-benzyl, acetylamino-benzyl, 1-phenylethyl, 2-phenylethyl, 2-hydroxy-1-phenylethyl, 1-(acetylamino-phenyl)ethyl, 2-(acetylamino-phenyl)ethyl, 1-hydroxy-3-phenylprop-2-yl, 1-hydroxy-1-phenylprop-2-yl, furylmethyl, thienylmethyl and pyridylmethyl. More particularly, $R^{11}$ and $R^{12}$ may independently represent hydrogen, methyl, acetyl or benzyl.

Specific compounds within the scope of the present invention include:
4-benzyl-2-hydroxymethyl-1-[3-(5-(1,2,4-triazol-4-yl)-1H-indol-3-yl)propyl]piperazine;
4-benzyl-3-hydroxymethyl-1-[3-(5-(1,2,4-triazol-4-yl)-1H-indol-3-yl)propyl]piperazine;
2-acetamidomethyl-4-benzyl-1-[3-(5-(1,2,4-triazol-4-yl)-1H-indol-3-yl)propyl]piperazine;
3-(N-benzylaminomethyl)-4-methyl-1-[3-(5-(1,2,4-triazol-4-yl)-1H-indol-3-yl)propyl]piperazine;
3-(N-benzyl-N-methylaminocarbonyl)-4-methyl-1-[3-(5-(1,2,4-triazol-4-yl) -1H-indol-3-yl)propyl]piperazine;
4-benzyl-3-(N,N-dimethylaminomethyl)-1-[3-(5-(1,2,4-triazol-4-yl)-1H -indol-3-yl)propyl]piperazine;
and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Typical unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of migraine, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

The compounds according to the invention wherein $R^a$ is other than hydrogen may be prepared by a process which comprises attachment of the $R^a$ moiety to a compound of formula III:

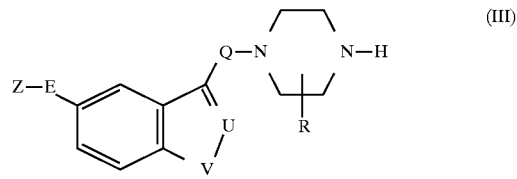

wherein Z, E, Q, U, V and R are as defined above.

Attachment of the $R^a$ moiety to the compounds of formula III may conveniently be effected by standard techniques such as alkylation. One example thereof comprises treatment with an aryl($C_{1-6}$)alkyl halide such as benzyl iodide, typically under basic conditions, e.g. sodium hydride or potassium carbonate in N,N-dimethylformamide, or triethylamine in acetonitrile. Another such example comprises treatment of the compound of formula III with an aryl($C_{1-6}$)alkyl mesylate such as 2-(4 -cyanophenyl)ethyl methanesulphonate, typically in the presence of sodium carbonate and sodium iodide, in a suitable solvent such as 1,2-dimethoxyethane.

Alternatively, the $R^a$ moiety may conveniently be attached by reductive alkylation. This approach suitably comprises treating the required compound of formula III as defined above with the appropriate aldehyde, e.g. formaldehyde, benzaldehyde, furfuraldehyde or thiophene carboxaldehyde, in the presence of a reducing agent such as sodium cyanoborohydride.

The compounds of formula III above wherein U represents C—$R^2$ and V represents N—$R^3$, corresponding to the indole derivatives of formula IC as defined above wherein $R^a$ is hydrogen, may be prepared by a process which comprises reacting a compound of formula IV:

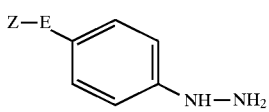

(IV)

wherein Z and E are as defined above; with a compound of formula V, or a carbonyl-protected form thereof:

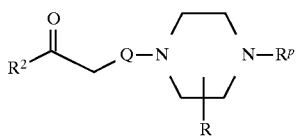

(V)

wherein R, R² and Q are as defined above, and R^P represents an amino-protecting group; followed, where required, by N-alkylation by standard methods to introduce the moiety R³; with subsequent removal of the amino-protecting group R^P.

The reaction between compounds IV and V, which is an example of the well-known Fischer indole synthesis, is suitably carried out by heating the reagents together under mildly acidic conditions, e.g. 4% sulphuric acid at reflux.

Suitable carbonyl-protected forms of the compounds of formula V include the dimethyl acetal or ketal derivatives.

The protecting group R^P in the compounds of formula V is suitably a carbamoyl moiety such as t-butoxycarbonyl (BOC), which can conveniently be removed as necessary by treatment under mildly acidic conditions. Indeed, the acidic conditions of the Fischer indole synthesis reaction will generally suffice to remove the BOC group.

The Fischer reaction between compounds IV and V may be carried out in a single step, or may proceed via an initial non-cyclising step at a lower temperature to give an intermediate of formula VI:

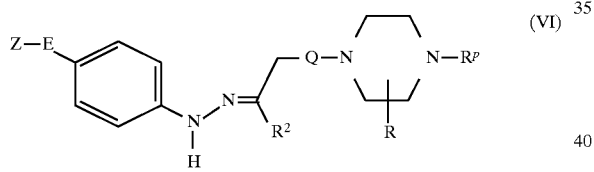

(VI)

wherein Z, E, Q, R, R² and R^P are as defined above; followed by cyclisation using a suitable reagent, e.g. a polyphosphate ester.

The intermediates of formula V, or carbonyl-protected forms thereof, may be prepared by reacting a compound of formula VII, or a carbonyl-protected form thereof, with a compound of formula VIII:

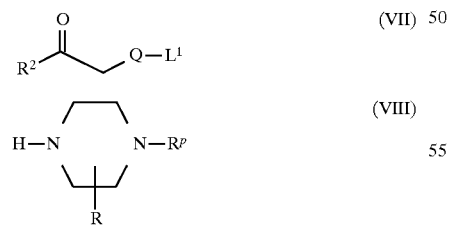

(VII)

(VIII)

wherein Q, R, R² and R^P are as defined above, and L¹ represents a suitable leaving group.

The leaving group L¹ is suitably a halogen atom, e.g. chlorine or bromine.

Where L¹ represents a halogen atom, the reaction between compounds VII and VIII is conveniently effected by stirring the reactants under basic conditions in a suitable solvent, for example potassium carbonate in N,N-dimethylformamide, or triethylamine in tetrahydrofuran or acetonitrile.

The compounds according to the invention wherein U represents C—R² and V represents N—R³—i.e. the indole derivatives of formula IC as defined above—may alternatively be prepared by a process which comprises reacting a compound of formula IV as defined above with a compound of formula IX, or a carbonyl-protected form thereof:

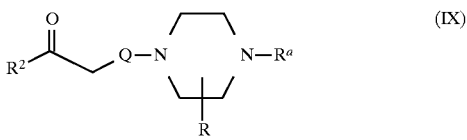

(IX)

wherein Q, R, R^a and R² are as defined above; under conditions analogous to those described above for the reaction between compounds IV and V; followed, where required, by N-alkylation by standard methods to introduce the moiety R³.

As for the compounds of formula V, suitable carbonyl-protected forms of the compounds of formula IX include the dimethyl acetal or ketal derivatives. Where the alkylene chain Q is substituted by a hydroxy group, this group may condense with the carbonyl moiety in compounds V and IX, whereby the carbonyl moiety is protected in the form of a cyclic hemiacetal.

As with that between compounds IV and V, the Fischer reaction between compounds IV and IX may be carried out in a single step, or may proceed via an initial non-cyclising step at a lower temperature to give an intermediate of formula X:

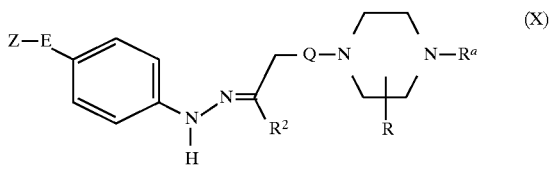

(X)

wherein Z, E, Q, R, R^a and R² are as defined above; followed by cyclisation using a suitable reagent, e.g. a polyphosphate ester.

The intermediates of formula IX, or carbonyl-protected forms thereof, may be prepared by reacting a compound of formula VII as defined above, or a carbonyl-protected form thereof, with a compound of formula XI:

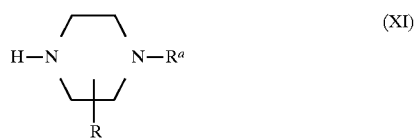

(XI)

wherein R and R^a are as defined above; under conditions analogous to those described above for the reaction between compounds VII and VIII.

In an alternative procedure, the compounds of formula III above may be prepared by a process which comprises reacting a compound of formula VIII as defined above with a compound of formula XII:

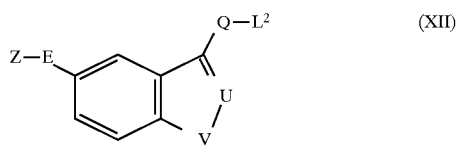

(XII)

wherein Z, E, Q, U and V are as defined above, and L² represents a suitable leaving group; followed by removal of the amino-protecting group R^P.

Similarly, the compounds of formula I as defined above may be prepared by a process which comprises reacting a compound of formula XI as defined above with a compound of formula XII as defined above.

The leaving group $L^2$ is suitably an alkylsulphonyloxy or arylsulphonyloxy group, e.g. methanesulphonyloxy (mesyloxy) or p-toluenesulphonyloxy (tosyloxy).

Where $L^2$ represents an alkylsulphonyloxy or arylsulphonyloxy group, the reaction between compound XII and compound VIII or XI is conveniently carried out in a suitable solvent such as 1,2-dimethoxyethane or isopropyl alcohol, typically in the presence of a base such as sodium carbonate or potassium carbonate, optionally with the addition of a catalytic amount of sodium iodide.

In one representative approach, the compounds of formula XII wherein U represents CH, V represents NH and $L^2$ represents a mesyloxy or tosyloxy group may be prepared by the sequence of steps illustrated in the following reaction scheme (cf. Larock and Yum, *J. Am. Chem. Soc.*, 1991, 113, 6689):

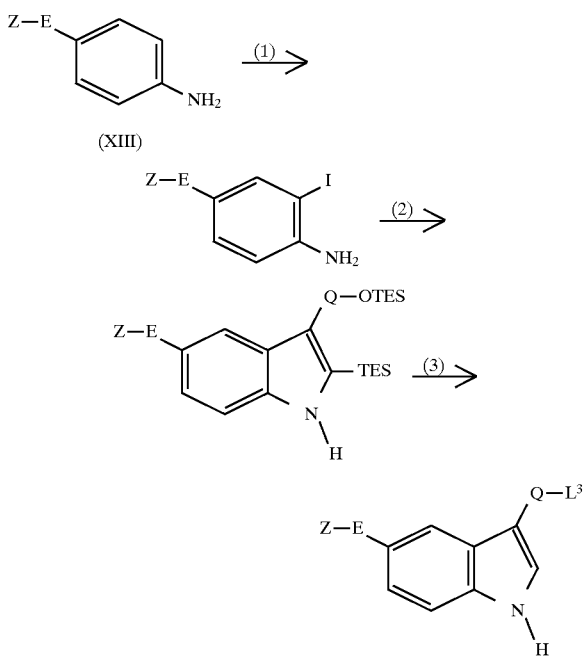

wherein Z, E and Q are as defined above, $L^3$ represents mesyloxy or tosyloxy, and TES is an abbreviation for triethylsilyl.

In Step 1 of the reaction scheme, the aniline derivative XIII is treated with iodine monochloride, typically in acetonitrile, in order to introduce an iodine atom ortho to the amine moiety. Step 2 involves a palladium-mediated coupling reaction with the protected acetylene derivative TES—C≡C—Q—OTES, typically using palladium acetate and triphenylphosphine in the presence of lithium chloride and sodium carbonate, suitably in N,N-dimethylformamide at an elevated temperature. This is followed in Step 3 by removal of the TES moiety, ideally in refluxing methanolic hydrochloric acid; followed in turn by mesylation or tosylation, suitably by using mesyl chloride or tosyl chloride respectively in the presence of a base such as triethylamine or pyridine, typically in dichloromethane/acetonitrile.

In another representative approach, the compounds of formula XII wherein U represents CH, V represents NH, Q represents a propylene chain and $L^2$ represents a mesyloxy or tosyloxy group may be prepared by reacting 3,4-dihydro-2H-pyran with a compound of formula IV as defined above or a salt thereof, under a variant of the Fischer reaction conditions as described above for the reaction between compounds IV and V; followed by mesylation or tosylation of the 3-hydroxypropyl-indole derivative thereby obtained, typically by treatment with mesyl chloride or tosyl chloride under standard conditions.

The Fischer reaction with 3,4-dihydro-2H-pyran is suitably brought about by heating the hydrazine derivative IV or an acid addition salt thereof, typically the hydrochloride salt, in an inert solvent such as dioxan, advantageously in the presence of a mineral acid such as hydrochloric acid or a Lewis acid such as zinc chloride, at the reflux temperature of the solvent.

In a further procedure, the compounds of formula III above wherein U represents nitrogen and V represents N—$R^3$, corresponding to the indazole derivatives of formula IB as defined above wherein $R^a$ is hydrogen, may be prepared by a process which comprises cyclising a compound of formula XIV:

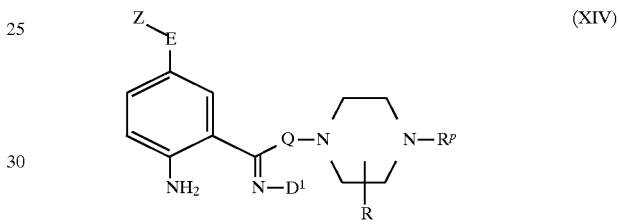

wherein Z, E, Q, R and $R^p$ are as defined above, and $D^1$ represents a readily displaceable group; followed, where required, by N-alkylation by standard methods to introduce the moiety $R^3$; with subsequent removal of the amino-protecting group $R^p$.

Similarly, the compounds of formula I wherein U represents nitrogen and V represents N—$R^3$—i.e. the indazole derivatives of formula IB as defined above—may be prepared by a process which comprises cyclising a compound of formula XV:

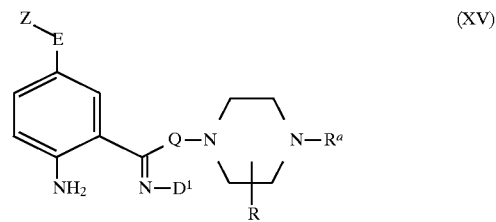

in which Z, E, Q, R, $R^a$ and $D^1$ are as defined above.

The cyclisation of compounds XIV and XV is conveniently achieved in a suitable organic solvent at an elevated temperature, for example in a mixture of m-xylene and 2,6-lutidine at a temperature in the region of 140° C.

The readily displaceable group $D^1$ in the compounds of formula XIV and XV suitably represents a $C_{1-4}$ alkanoyloxy group, preferably acetoxy. Where $D^1$ represents acetoxy, the desired compound of formula XIV or XV may be conveniently prepared by treating a carbonyl compound of formula XVI:

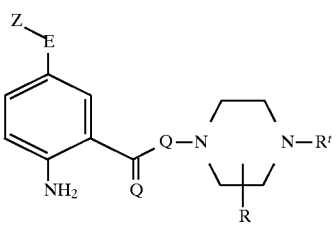

(XVI)

wherein Z, E, Q and R are as defined above, and R$^t$ corresponds to the group R$^a$ as defined above, or R$^t$ represents an amino-protecting group as defined for R$^p$; or a protected derivative thereof, preferably the N-formyl protected derivative; with hydroxylamine hydrochloride, advantageously in pyridine at the reflux temperature of the solvent; followed by acetylation with acetic anhydride, advantageously in the presence of a catalytic quantity of 4-dimethylaminopyridine, in dichloromethane at room temperature.

The N-formyl protected derivatives of the intermediates of formula XVI may conveniently be prepared by ozonolysis of the corresponding indole derivative of formula XVII:

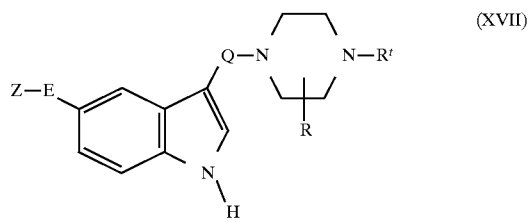

(XVII)

wherein Z, E, Q, R and R$^t$ are as defined above; followed by a reductive work-up, advantageously using dimethylsulphide.

The indole derivatives of formula XVII may be prepared by methods analogous to those described in the accompanying Examples, or by procedures well known from the art.

In a still further procedure, the compounds of formula III above wherein U represents C—R$^2$ and V represents oxygen or sulphur, corresponding to the benzofuran or benzthiophene derivatives of formula IA wherein V is oxygen or sulphur respectively and R$^a$ is hydrogen, may be prepared by a process which comprises cyclising a compound of formula XVIII:

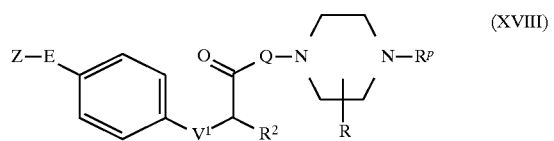

(XVIII)

wherein Z, E, Q, R, R$^2$ and R$^p$ are as defined above, and V$^1$ represents oxygen or sulphur; followed by removal of the amino-protecting group R$^p$.

Similarly, the compounds of formula I wherein U represents C—R$^2$ and V represents oxygen or sulphur—i.e. the benzofuran or benzthiophene derivatives of formula IA above—may be prepared by a process which comprises cyclising a compound of formula XIX:

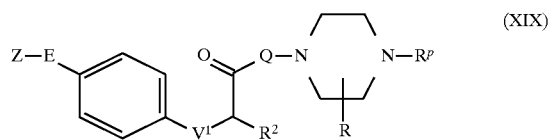

(XIX)

wherein Z, E, Q, R, R$^a$, R$^2$ and V$^1$ are as defined above.

The cyclisation of compounds XVIII and XIX is conveniently effected by using polyphosphoric acid or a polyphosphate ester, advantageously at an elevated temperature.

The compounds of formula XVIII and XIX may be prepared by reacting a compound of formula XX with a compound of formula XXI:

(XX)

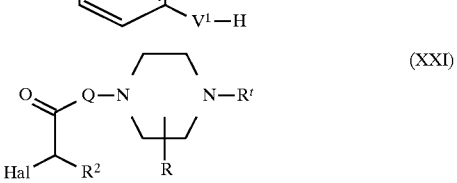

(XXI)

wherein Z, E, Q, R, R$^2$, V$^1$ and R$^t$ are as defined above, and Hal represents a halogen atom.

The reaction is conveniently effected in the presence of a base such as sodium hydroxide.

The hydroxy and mercapto derivatives of formula XX may be prepared by a variety of methods which will be readily apparent to those skilled in the art. One such method is described in EP-A-0497512.

The hydrazine derivatives of formula IV above may be prepared by methods analogous to those described in EP-A-0438230 and EP-A-0497512, as also may the aniline derivatives of formula XII.

Where they are not commercially available, the starting materials of formula VII, VIII, XI and XXI may be prepared by methods analogous to those described in the accompanying Examples, or by standard procedures well known from the art.

It will be understood that any compound of formula I initially obtained from any of the above processes may, where appropriate, subsequently be elaborated into a further compound of formula I by techniques known from the art. For example, a compound of formula I wherein R is hydroxymethyl initially obtained may be mesylated using methanesulphonyl chloride, and the methyl group subsequently displaced with ammonia to afford the corresponding compound of formula I wherein R represents aminomethyl; this compound may in turn be acylated using a lower acyl halide, e.g. acetyl chloride, suitably in an organic base such as triethylamine, whereby a compound of formula I in which R represents an acylaminomethyl group, such as acetamidomethyl, may be obtained. In addition, a compound of formula I initially obtained wherein R represents a group of formula —CONR$^x$R$^y$ initially obtained may be converted into the corresponding compound of formula I wherein R represents —CH$_2$NR$^x$R$^y$ by treatment under standard conditions with an appropriate reducing agent, e.g. borane-tetrahydrofuran. By way of further illustration, a compound of formula I wherein R$^a$ is benzyl initially obtained may be converted by catalytic hydrogenation to the corresponding compound of formula III, which in turn may be converted into a further compound of formula I using, for example, standard N-alkylation techniques as described above. Furthermore, a compound of formula I initially obtained wherein the R$^a$ moiety is substituted by nitro may be converted by catalytic hydrogenation to the corresponding amino-substituted compound. This amine may then, for example, be N-acylated using the appropriate acyl halide, e.g. acetyl chloride; or aminocarbonylated, using potassium isocyanate, to the corresponding urea derivative; or converted to a 1,2,4-triazol-4-yl derivative using N,N-dimethylformamide azine. Moreover, a compound of formula I wherein $R^3$ is hydrogen initially obtained may be converted into a compound of formula I wherein $R^3$ represents $C_{1-6}$ alkyl by standard alkylation techniques, for example by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The novel compounds may be prepared in racemic form, or individual enantiomers may be prepared either by enantiospecific synthesis or by resolution. The novel compounds may, for example, be resolved into their component enantiomers by standard techniques such as preparative HPLC, or the formation of diastereomeric pairs by salt formation with an optically active acid, such as (−)-di-p-toluoyl-d-tartaric acid and/or (+)-di-p-toluoyl-1-tartaric acid, followed by fractional crystallization and regeneration of the free base. The novel compounds may also be resolved by formation of diastereomeric esters or amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protectiue Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Examples illustrate the preparation of compounds according to the invention.

The compounds in accordance with the present invention potently and selectively bind to the 5-$HT_{1D\alpha}$ receptor subtype, inhibit forskolin-stumulated adenylyl cyclase activity, and stimulate [$^{35}$S]-GTPγS binding to membranes from clonal cell lines expressing human cloned receptors.

5-$HT_{1D\alpha}$/5-$HT_{1D\beta}$ Radioligand Binding

Chinese hamster ovary (CHO) clonal cell lines expressing the human 5-$HT_{1D\alpha}$ and 5-$HT_{1D\beta}$ receptors were harvested in PBS and homogenised in ice cold 50 mM Tris-HCl (pH 7.7 at room temperature) with a Kinematica polytron and centrifuged at 48,000 g at 4° C. for 11 min. The pellet was then resuspended in 50 mM Tris-HCl followed by a 10 min incubation at 37° C. Finally the tissue was recentrifuged at 48,000 g, 4° C. for 11 imin and the pellet resuspended, in assay buffer (composition in mM: Tris-HCl 50, pargyline 0.01, $CaCl_2$4; ascorbate 0.1%; pH 7.7 at room temperature) to give the required volume immediately prior to use (0.2 mg protein/ml). Incubations were carried out for 30 min at 37° C. in the presence of 0.02–150 nM [$^3$H]-5-HT for saturation studies or 2–5 nM [$^3$H]-5-HT for displacement studies. The final assay volume was 1 ml. 5-HT (10 μM) was used to define non-specific binding. The reaction was initiated by the addition of membrane and was terminated by rapid filtration through Whatman GF/B filters (presoaked in 0.3% PEI/ 0.5% Triton X) followed by 2×4 ml washings with 50 mM Tris-HCl. The radioactive filters were then counted on a LKB beta or a Wallac beta plate counter. Binding parameters were determined by non-linear, least squares regression analysis using an iterative curve fitting routine, from which $IC_{50}$ (the molar concentration of compound necessary to inhibit binding by 50%) values could be calculated for each test compound. The $IC_{50}$ values for binding to the 5-$HT_{1D\alpha}$ receptor subtype obtained for the compounds of the accompanying Examples were below 50 nM in each case. Furthermore, the compounds of the accompanying Examples were all found to possess a selective affinity for the 5-$HT_{1D\alpha}$ receptor subtype of at least 10-fold relative to the 5-$HT_{1D\beta}$ subtype.

5-$HT_{1D\alpha}$/5-$HT_{1D\beta}$ Adenylyl Cyclase Assay

Studies were performed essentially as described in *J. Pharmacol. Exp. Ther.*, 1986, 238, 248. CHO clonal cell lines expressing the human cloned 5-$HT_{1D\alpha}$ and 5-$HT_{1D\beta}$ receptors were harvested in PBS and homogenised, using a motor driven teflon/glass homogeniser, in ice cold Tris HCl-EGTA buffer (composition in mM: Tris HCl 10, EGTA 1, pH 8.0 at room temperature) and incubated on ice for 30–60 min. The tissue was then centrifuged at 20,000 g for 20 min at 4° C., the supernatant discarded and the pellet resuspended in Tris HCl-EDTA buffer (composition in mM: Tris HCl 50, EDTA 5, pH 7.6 at room temperature) just prior to assay. The adenylyl cyclase activity was determined by measuring the conversion of α-[$^{33}$P]-ATP to [$^{33}$P]-cyclic AMP. A 10 μl aliquot of the membrane suspension was incubated, for 10–15 min, in a final volume of 50 μl, at 30° C., with or without forskolin (10 μM), in the presence or absence of test compound. The incubation buffer consisted of 50 mM Tris HCl (pH 7.6 at room temperature), 100 mM NaCl, 30 μM GTP, 50 μM cyclic AMP, 1 mM dithiothreitol, 1 mM ATP, 5 mM $MgCl_2$, 1 mM EGTA, 1 mM 3-isobutyl-1-methylxanthine, 3.5 mM creatinine phosphate, 0.2 mg/ml creatine phosphokinase, 0.5–1 μCi α-[$^{33}$P]-ATP and 1 nCi [$^3$H]-cyclic AMP. The incubation was initiated by the addition of membrane, following a 5 min preincubation at 30° C., and was terminated by the addition of 100 μl SDS (composition in mM: sodium lauryl sulphate 2%, ATP 45, cyclic AMP 1.3, pH 7.5 at room temperature). The ATP and cyclic AMP were separated on a double column chromatography system (*Anal. Biochem.*, 1974, 58, 541). Functional parameters were determined using a least squares curve fitting programme ALLFIT (*Am. J. Physiol.*, 1978, 235, E97) from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-$HT_{1D\alpha}$ receptor obtained for the compounds of the accompanying Examples were below 500 nM in each case. Moreover, the compounds of the accompanying Examples which were tested were all found to possess at least a 10-fold selectivity for the 5-$HT_{1D\alpha}$ receptor subtype relative to the 5-$HT_{1D\beta}$ subtype.

5-$HT_{1D\alpha}$/5-$HT_{1D\beta}$ GTPγS Binding

Studies were performed essentially as described in *Br. J. Pharmacol.*, 1993, 109, 1120. CHO clonal cell lines expressing the human cloned 5-$HT_{1D\alpha}$ and 5-$HT_{1D\beta}$ receptors were harvested in PBS and homogenised using a Kinematica polytron in ice cold 20 mM HEPES containing 10 mM EDTA, pH 7.4 at room temperature. The membranes were then centrifuged at 40,000 g, 4° C. for 15 min. The pellet was then resuspended in ice cold 20 mM HEPES containing 0.1 mM EDTA, pH 7.4 at room temperature and recentrifuged at 40,000 g, 4° C. for 15–25 minutes. The membranes were then resuspended in assay buffer (composition in mM: HEPES 20, NaCl 100, $MgCl_2$10, pargyline 0.01; ascorbate 0.1%; pH 7.4 at room temperature) at a concentration of 40 μg protein/ml for the 5-$HT_{1D\alpha}$ receptor transfected cells and 40–50 μg protein/ml for the 5-$HT_{1D\beta}$ receptor transfected cells. The membrane suspension was then incubated, in a volume of 1 ml, with GDP (100 μM for 5-$HT_{1D\alpha}$ receptor transfected cells, 30 μM for the 5-$HT_{1D\beta}$ receptor transfected cells) and test compound at 30° C. for 20 min and then transferred to ice for a further 15 min. [$^{35}$S]-GTPγS was then added at a final concentration of 100 pM and the samples incubated for 30 min at 30° C. The reaction was initiated by the addition of membrane and was terminated by rapid filtration through Whatman GF/B filters and washed with 5 ml water. The radioactive filters were then counted on a LKB beta counter. Functional parameters were determined by a non-linear, least squares regression analysis using an iterative curve fitting routine, from which $E_{max}$ (maximal effect) and $EC_{50}$ (the molar concentration of compound necessary to inhibit the maximal effect by 50%) values were obtained for each test compound. Of those compounds which were tested in this assay, the $EC_{50}$ values for the 5-HT$_{1D\alpha}$ receptor obtained for the compounds of the accompanying Examples were below 500 nM in each case. Moreover, the compounds of the accompanying Examples which were tested were all found to possess at least a 10-fold selectivity for the 5-HT$_{1D\alpha}$ receptor subtype relative to the 5-HT$_{1D\beta}$ subtype.

EXAMPLE 1

4-Benzyl-2-hydroxymethyl-1-[3-(5-(1,2,4-triazol-4-yl)-1H-indol-3-yl)propyl]piperazine 1.3 Hydroyen Oxalate 1. Intermediate 1: Piperazine-2-carboxylic acid ethyl ester trifluoroacetic acid salt
Step 1: N,N'-Di-tert-butyloxycarbonylpiperazine-2-carboxylic acid To a stirred solution of piperazine-2-carboxylic acid dihydrochloride (10 g, 0.049 mol) in dioxan/water (1:1; 400 mL) was added Na$_2$CO$_3$ (31 g, 0.249 mol) and di-tert-butyl dicarbonate (23.6 g, 0.11 mol) at room temperature. The mixture was stirred for 36 h then the solution was adjusted to pH7 with 5M HCl. The solvents were evaporated in vacuo and the residue chromatographed on silica gel, using CH$_2$Cl$_2$:MeOH:AcOH (90:10:1), to afford the title compound (14.95 g; 92%) as a colourless solid.

mp 231–233° C. $^1$H NMR (360 MHz,CDCl$_3$) δ 1.44 (9H, s), 2.80–2.94 (1H, m), 3.05–3.30 (2H, m), 3.72–4.10 (2H, m), 4.52–4.80 (2H, m).

Step 2: N,N'-Di-tert-butyloxycarbonylpiperazine-2-carboxylic acid ethyl ester

To a stirred solution of N,N'-di-tert-butyloxycarbonylpiperazine-2-carboxylic acid (4.6 g, 0.013 mol), 1-(3-(dimethylamino)propyl)-3-ethylcarbodiimide hydrochloride (3.2 g, 0.016 mol), triethylamine (2.2 mL, 0.016 mol) and 4-pyrrolidinopyridine (0.23 g, 1.5 mmol) in CH$_2$Cl$_2$ (120 mL) was added ethanol (0.93 mL, 0.016 mol). The mixture was left stirring overnight, then the mixture was washed with water (2×50 mL), 5% aqueous acetic acid (2×300 mL) and water (2×50 mL). The organic phase was separated, dried (Na$_2$SO$_4$) and evaporated. The residue was chromatographed on silica gel, eluting with petrol:EtOAc (1:1) to give the ester (3.3 g, 72%) as a colourless oil. $^1$H NMR (360 MHz, CDCl$_3$) δ 1.28 (3H, t, J=7.1 Hz), 1.44 (9H, s), 2.70–3.32 (3H, m), 3.70–4.12 (2H, m), 4.14–4.26 (2H, m), 4.46–4.76 (2H, m). MS (ES$^+$) 359 (M+1).

Step 3: Piperazine-2-carboxylic acid ethyl ester trifluoroacetic acid salt

A solution of N,N'-di-tert-butyloxycarbonylpiperazine-2-carboxylic acid ethyl ester (6.9 g, 0.019 mol) and trifluoroacetic acid (34 mL) in CH$_2$Cl$_2$ (340 mL) was stirred at room temperature for 7 h. The solvents were removed in vacuo and the residue azeotroped with toluene (2×100 mL) and ether (2×100 mL). The resultant colourless solid (7.1 g, 95%) was triturated with ether and collected by filtration. mp 185°–187° C. $^1$H NMR (360 MHz, d$_6$-DMSO) δ 1.25 (3H, t, J=7.1 Hz), 3.04–3.18 (2H, m), 3.22–3.29 (1H, m), 3.39–3.46 (2H, m), 3.65 (1H, dd, J=13.1 and 3.5 Hz), 4.25 (2H, q, J=7.1 Hz 4.33 (1H, dd, J=10.8 and 3.5 Hz). ps 2. Intermediate 2: 5-Chloronentanal dimethyl acetal A solution of 5-chlorovaleryl chloride (23.7 g, 0.15 mol) in THF (500 mL) was cooled to −78° C. and a solution of lithium tri(tert-butoxy)-aluminium hydride in THF (183.2 mL of a 1M solution, 0.18 mol) was added dropwise over a period of 5 h. The solution was stirred at −78° C. for 16 h, then the reaction mixture was quenched with 1M HCl. The mixture was allowed to warm to room temperature and then extracted with ether (3×200 mL). The combined organic layers were washed with sat. K$_2$CO$_3$ solution, water and brine then dried (Na$_2$SO$_4$). The filtrate was evaporated in vacuo to afford the aldehyde, as a colourless oil, which was used without further purification.

The aldehyde was dissolved in methanol (150 mL) and conc. H$_2$SO$_4$ (0.5 mL) and stirred overnight at room temperature. The solvents were removed in vacuo and the residue dissolved in ether. The organic layer was washed with sat. NaHCO$_3$ solution, water and brine. The organic layer was then dried (Na$_2$SO$_4$) and evaporated. The residue was chromatographed on silica gel, eluting with hexane:ether (90:10), to afford the title compound (12.15 g, 49%) as a colourless oil. $^1$H NMR (360 MHz, CDCl$_3$) δ 1.46–1.66 (4H, m), 1.78–1.85 (2H,m), 3.32 (6H, s), 3.52–3.78 (2H, m), 4.36 (1H, t, J=5.6 Hz).

3. 4-Benzyl-2-hydroxymethylpiperazine

To a cooled (0° C.) and stirred solution of Intermediate 1 (22 g, 57 mmol), acetic acid (9.7 mL, 171 mmol) and sodium cyanoborohydride (7.16 g, 114 mmol) in methanol (440 mL) was added benzaldehyde (5.8 mL, 57 mmol). The cooling bath was removed and the mixture stirred at room temperature for 3 h. Saturated K$_2$CO$_3$ solution (200 mL) was added and the mixture stirred for 15 min. The solvents were evaporated and the residue partitioned between CH$_2$Cl$_2$ (2×400 mL) and water (500 mL). The combined organic layers were dried (Na$_2$SO$_4$) and evaporated. The residue was chromatographed on silica gel, eluting with CH$_2$Cl$_2$: MeOH (95:5) to afford an inseparable mixture of 4-benzylpiperazine-2-carboxylic acid methyl ester and the corresponding ethyl ester (5.33 g, 40%), in a 7:1 ratio respectively.

To a solution of the esters (5.33 g, 22.8 mmol) in THF (200 mL) was added LiAl H$_4$ (22.8 mL of a 1.0M solution in ether) dropwise at −10° C. Stirring was continued at −10° C. for 2.5 h. After this time saturated Na$_2$SO$_4$ solution (30 mL) was added and the cooling bath removed. Stirring was continued at room temperature for 10 min then the mixture was filtered and the filtrate evaporated. The residue was chromatographed on silica gel, eluting with CH$_2$Cl$_2$:MeOH:NH$_3$ (90:8:1→60:8:1) to afford the title compound (3.7 g, 78%) as a colourless oil. $^1$H NMR (360 MHz, CDCl$_3$) δ 1.89–1.95 (1H, m), 2.08–2.30 (3H, m), 2.68–2.71 (2H, m), 2.86–3.04 (3H, m), 3.45–3.60 (4H, m), 7.13–7.32 (5H, m). MS (ES$^+$) 207 (M+1).

4. 4-Benzyl-2-hydroxymethyl-1-(5,5-dimethoxypentyl) piperazine

A mixture of 4-benzyl-2-hydroxymethylpiperazine (2.0 g, 9.7 mmol), Intermediate 2 (2.0 g, 12.1 mmol), Na$_2$CO$_3$ (1.54 g, 14.6 mmol) and sodium iodide (1.6 g, 10.7 mmol) in 1,2-dimethoxyethane (30 mL) was heated at reflux for 12 h. After this time the mixture was filtered and the filtrate evaporated. The residue was partitioned between CH$_2$Cl$_2$ (30 mL) and water (30 mL). The organic phase was separated, dried (Na$_2$SO$_4$) and evaporated. The residue was chromatographed on silica gel, eluting with CH$_2$Cl$_2$:MeOH (93:7), to afford the piperazine (2.19 g, 67%) as an orange oil. $^1$H NMR (360 MHz, CDCl$_3$) δ 1.33–1.65 (6H, m), 2.41–2.77 (8H, m), 3.00–3.06 (1H, m), 3.31 (6H, s), 3.48 (2H, s), 3.53 (1H, d, J=10.8 Hz), 3.91 (1H, dd, J=11.3 and 3.0 Hz), 4.35 (1H, t, J=5.7 Hz), 7.24–7.34 (5H, m). MS (ES$^+$) 337(M+1).

5. 4-Benzyl-2-hydroxymethyl-1-[3-(5-(1,2,4-triazol-4-yl)-1H-indol-3-yl)propyl]piperazine oxalate A mixture of 4-benzyl-2-hydroxymethyl-1-(5,5-dimethoxypentyl)piperazine (245 mg, 0.73 mmol) and 4-(1,2,4-triazol-4-yl)phenylhydrazine (127 mg, 0.73 mmol) in 4% H$_2$SO$_4$ (8 mL) was heated at reflux overnight. The solution was basified using sat. K$_2$CO$_3$ solution and extracted with $^n$BuOH (2×30 mL). The combined organic layers were evaporated and the residue chromatographed on silica gel, eluting with CH$_2$Cl$_2$:MeOH:NH$_3$ (90:10:1). The title compound (73 mg, 23%) was isolated as a pale yellow foam. The free base was converted to the oxalate salt by treatment with oxalic acid in methanol/water. mp 130°–132° C. Found: C, 59.90; H, 6.18; N, 15.35%. C$_{25}$H$_{30}$N$_6$O. 1.3 (C$_2$H$_2$O$_4$). 0.3 (H$_2$O). 0.1 (Et$_2$O) requires C, 60.01; H, 6.15; N, 15.00%. $^1$H NMR (360 MHz, d$_6$-DMSO) δ 1.92–2.10 (2H, m), 2.36–2.46 (2H, m), 2.70–3.06 (6H, m), 3.14–3.36 (3H, m), 3.57–3.72 (4H, m), 7.24–7.40 (7H, m), 7.49 (1H, d, J=8.6 Hz), 7.79 (1H, s), 8.99 (2H, s), 11.19 (1H, br s).

EXAMPLE 2

2-Acetamidomethyl-4-benzyl-1-[3-(5-(1,2,4-triazol-4-yl)-1H-indol-3-yl)propyl]piperazine 1.6 Hydrogen Oxalate 1. 2-Aminomethyl-4-benzyl-1-[3-(5-(1,2,4-triazol-4-yl)-1H-indol-3-yl)propyl]piperazine To a stirred solution of 4-benzyl-2-hydroxymethyl-1-[3-(5-(1,2,4-triazol-4-yl)-1H-indol-3-yl)propyl]piperazine (110 mg, 0.23 mmol) and triethylamine (64 μL, 0.46 mmol) in THF (3 mL) at −100° C., was added methanesulphonyl chloride (374 μL, 0.46 mmol) dropwise. The cooling bath was removed and the mixture stirred at 25° C. for 30 min. After this time the mixture was diluted with EtOAc (30 mL) and washed with sat. NaHCO$_3$ solution (20 mL). The organic layer was separated, dried (Na$_2$SO$_4$) and evaporated. The crude mesylate, which was isolated as a pale yellow foam, was used directly in the subsequent reaction.

The mesylate was dissolved in methanolic ammonia (5 mL of a 2.0M solution) and the solution heated at 80° C. in a sealed tube. After 6 h the solvent was removed in vacuo and the residue partitioned between n-butanol (10 mL) and sat. NaHCO$_3$ solution (10 mL). The organic layer was separated and evaporated. The residue was chromatographed on silica gel, eluting with CH$_2$Cl$_2$:MeOH: NH$_3$ (60:8:1), to afford the amine (54 mg, 54%) as a pale yellow oil. $^1$H NMR (360 MHz, CDCl$_3$) δ 1.81–1.88 (2H, m), 2.13–2.20 (2H, m), 2.31–2.37 (3H, m), 2.57–2.85 (8H, m), 3.3 (1H, d, J=13 Hz), 3.44 (1H, d, J=13 Hz), 7.05–7.08 (2H, m), 7.16–7.24 (5H,m), 7.39 (1H, d, J=8.5 Hz), 7.48 (1H, d, J=2 Hz), 8.40 (2H, s), 8.52 (1H, br s).

2. 2-Acetamidomethyl-4-benzyl-1-[3-(5-(1,2,4-triazol-4-yl)-1H-indol-3- yl)propyl]piperazine oxalate To a stirred solution of the amine (47 mg, 0.11 mmol) in CH$_2$Cl$_2$ (3 mL) at 0° C. was added acetyl chloride (0.16 mL of a 0.7M solution in CH$_2$Cl$_2$,0.11 mmol) followed by triethylamine (15 μL, 0.11 mmol). The cooling bath was removed and the solution stirred at 25° C. for 1 h. After this time the solution was diluted with CH$_2$Cl$_2$ (10 mL) and washed with sat. NaHCO$_3$ solution (10 mL). The organic phase was separated, dried (Na$_2$SO$_4$) and evaporated. The residue was chromatographed on silica gel, eluting with CH$_2$Cl$_2$:MeOH (90:10), to afford the acetamide (18 mg, 35%) as a colourless oil. The free base was converted to the oxalate salt by treatment with oxalic acid in methanol/water. mp. 127° C. Found: C, 58.87; H, 6.26; N, 15.93%. C$_{27}$H$_{33}$N$_7$O. 1.6 (C$_2$H$_2$O$_4$) requires C, 58.92; H, 5.93; N, 15.93%. $^1$H NMR (360 MHz, d$_6$-DMSO) δ 1.80 (3H, s), 1.82–2.10 (2H, m), 2.36–3.30 (11H, m), 3.40–3.48 (2H, m), 3.62 (2H, br s), 7.29–7.35 (7H, m), 7.48 (1H, d, J=8.6 Hz), 7.82 (1H, s), 8.05 (1H, br s), 9.03 (2H, s), 11.13 (1H, brs).

EXAMPLE 3

4-Benzyl-3-hydroxymethyl-1-[3-(5-(1,2,4-triazol-4-yl)-1H-indol-3-yl)propyl]piperazine Oxalate Step 1: 3-[5-(1,2,4-Triazol-4-yl)-1H-indol-3-yl]propan-1-ol]

A solution of 4-(1,2,4-triazol-4-yl)phenylhydrazine (25 g, 143 mmol) in dioxan (250 mL) was treated with dihydropyran (24 g, 286 mmol) followed by 1M hydrochloric acid (150 mL) and heated at reflux for 18 h. The reaction mixture was evaporated, treated with toluene then re-evaporated. Inorganic solids were removed by treating the residue with a mixture of methanol and acetonitrile. The mother liquors were purified by column chromatography on silica using dichloromethane:methanol (9:1→4:1) as the eluant. The compound was recrystallised from acetonitrile to afford the title compound as a colourless solid (10.24 g, 30%); mp 205°–207° C. Found: C, 64.37; H, 5.76; N, 22.83%. C$_{13}$H$_{14}$N$_4$O requires: C, 64.45; H, 5.82; N, 23.13%. $^1$H NMR (360 MHz, d$_6$-DMSO) δ 1.81 (2H, q, J=7 Hz), 2.75 (2H, t, J=8 Hz), 3.46 (2H, dt, J=6.0 and 5.0 Hz), 4.43 (1H, t, J=5 Hz), 7.26 (1H, d, J=2 Hz), 7.29 (1H, dd, J=9.0 and 2.0 Hz), 7.47 (1H J=9 Hz), 7.77 (1H, d, J=2 Hz), 9.01 (2H, s), 11.05 (1H, br s). MS (CI$^+$) 243 (M+1).

Step 2: 4-tert-Butyloxycarbonyl-3-hydroxymethyl-1-[3-(5-(1,2,4-triazol-4-yl)-H-indol-3-yl)propyl]piperazine To a suspension of 3-[5-(1,2,4-triazol-4-yl)-1H-indol-3-yl]propan-1-ol](0.242 g, 1 mmol) in THF (30 mL) was added triethylamine (0.28 mL, 2 mmol), followed by methanesulphonyl chloride (0.15 mL, 2 mmol) and this mixture was stirred at room temperature under nitrogen for 1.5 h. The reaction mixture was filtered and the solvent evaporated. The residue was partitioned between CH$_2$Cl$_2$ (50 mL) and water (30 mL). The organic phase was washed with brine (30 mL), dried (Na$_2$SO$_4$) and evaporated to give the mesylate as a yellow oil which was used without further purification. To a solution of Intermediate 1 (0.772 g, 2 mmol) in dry DMF (4 mL) at 50° C. was added potassium carbonate (483 mg, 3.5 mmol) and dropwise, over a period of 10 min, a solution of the mesylate in dry DMF (3 mL). This mixture was heated at 80° C. for 2.5 h. The mixture was allowed to cool and then partitioned between CH$_2$Cl$_2$ (25 mL) and water (25 mL). The two layers were separated and the aqueous extracted with CH2Cl$_2$ (2×20 mL) and the combined organics were dried (Na$_2$SO$_4$) and evaporated. The residue was chromatographed on silica, eluting with 90:10:1 CH$_2$Cl$_2$:MeOH:NH$_3$, to afford the crude piperazine-indole contaminated with starting reagents.

The crude piperazine was redissolved in CH$_2$Cl$_2$ (20 mL) and di-tert-butyl dicarbonate (0.56 g, 2.6 mmol) was added. This mixture was stirred at room temperature for 1 h. The solvent was evaporated in vacuo and the residue chromatographed on silica, eluting with EtOAc: petrol (1:1) followed by CH$_2$Cl$_2$:MeOH (95:5) to afford 4-tert-butyloxycarbonyl-1-[3-(5-(1,2,4-triazol-4-yl)-1H-indol-3-yl)propyl] piperazine-3-carboxylic acid ethyl ester, contaminated with a small amount of the 2-isomer. This mixture was used without further purification in the next reaction.

To a solution of the esters (0.153 g, 0.32 mmol) in THF (5 mL) at −10° C. was added lithium aluminium hydride (0.32 mL of a 1M solution, 0.32 mmol) dropwise. The mixture was stirred at −10° C. for 1 h and then the reaction mixture was treated with sat. $Na_2SO_4$ solution (0.8 mL) and the mixture allowed to warm to room temperature over a period of 15 min. The resultant solid was removed by filtration and the filtrate was evaporated in vacuo. The residue was chromatographed on silica gel, eluting with $CH_2Cl_2$:MeOH (9:1), to afford the title compound (89 mg, 64%) as a colourless foam. $^1$H NMR (360 MHz, $CDCl_3$) δ 1.46 (9H, s), 1.90–1.99 (2H, m), 2.03–2.16 (1H, m), 2.28–2.36 (1H, m), 2.40–2.50 (2H, m), 2.78–2.94 (3H, m), 3.06–3.13 (1H, m), 3.37–3.48 (1H, m), 3.87–4.16 (4H, m), 7.14–7.20 (2H, m), 7.48 (1H, d, J=8.5 Hz), 7.57 (1H, d, J=2 Hz), 8.40 (1H, br s), 8.48 (2H, s).

Step 3: 3-Hydroxymethyl-4(H)-1-[3-(5-(1,2,4-triazol-4-yl)-1H-indol-3-yl)propyl]piperazine To a solution of 4-tert-butyloxycarbonyl-3-hydroxymethyl-1-[3-(5-(1,2,4-triazol-4-yl)-1H-indol-3-yl)propyl]piperazine (80 mg, 0.18 mmol) in $CH_2Cl_2$ (10 mL) was added trifluoroacetic acid (1 mL) dropwise. The solution was stirred at room temperature for 3 h. The solvent was evaporated in vacuo and the residue was azeotroped with toluene (2×10 mL). The residue was partitioned between $Na_2CO_3$ solution (10%, 20 mL) and n-butanol (20 mL). The organic phase was evaporated in vacuo and the residue chromatographed on silica gel with $CH_2Cl_2$:MeOH:$NH_3$ (80:20:2), to afford the title compound (61 mg, 99%) as a yellow gum. 1H NMR (250 MHz, $d_4$-MeOH) δ 1.89–2.03 (2H, m), 2.23–2.45 (2H, m), 2.55–2.63 (2H, m), 2.83–2.90 (2H, m), 3.03–3.19 (3H, m), 3.25–3.38 (2H, m), 3.56–3.63 (1H, m), 3.70–3.76 (1H, m), 7.23 (1H, s), 7.28 (1H, dd, J=8.6 and 2.1 Hz), 7.52 (1H, d, J=8.6 Hz), 7.76 (1H, d, J=2.1 Hz), 8.94 (2H, s).

Step 4: 4-Benzyl-3-hydroxymethyl-1-[3-(5-(1,2,4-triazol-4-yl)-1H-indol-3-yl)propyl]piperazine Oxalate To a solution of 3-hydroxymethyl-4(H)-1-[3-(5-(1,2,4-triazol-4-yl) -1H-indol-3-yl)propyl]piperazine (61 mg, 0.18 mmol) in MeOH (5 mL) was added acetic acid (3 μL, 0.54 mmol), sodium cyanoborohydride (22.5 mg, 0.36 mmol) and benzaldehyde (18 μL, 0.18 mmol). This mixture was stirred at room temperature under nitrogen for 4 h. Further sodium cyanoborohydride (11 mg, 0.18 mmol) and benzaldehyde (9 μL, 0.09 mmol) were added and the mixture stirred for 2 h. Further acetic acid (10 μL, 0.18 mmol), sodium cyanoborohydride (11 mg, 0.18 mmol) and benzaldehyde (9 μL, 0.09 mmol) were added and the mixture stirred for 16 h. Sat. $K_2CO_3$ solution (10 mL) was added and the solvents removed in vacuo. The residue was partitioned between n-butanol (20 mL) and water (20 mL). The organic phase was evaporated and the residue chromatographed on silica gel, eluting with $CH_2Cl_2$:MeOH:$NH_3$ (90:10:1→80:20:2), to afford the title compound (24 mg, 31%) as a colourless gum. The free base was converted to the oxalate salt by treatment with oxalic acid in methanol/ether. mp 105° C. (dec.). Found: C, 60.34; H, 6.20; N, 15.64% $C_{25}H_{30}N_6O$. ($C_2H_2O_4$). $H_2O$ requires: C, 60.21; H, 6.36; N, 15.60. $^1$H NMR (360 MHz, $d_6$-DMSO) δ 1.90–2.02 (2H, m), 2.30–2.44 (1H, m), 2.60–2.96 (9H, m), 3.02–3.42 (2H, m), 3.52–3.62 (1H, m), 3.68–3.74 (1H, m), 4.06–4.14 (1H, m), 7.22–7.37 (7H, m), 7.49 (1H, d, J=8.6 Hz), 7.78 (1H, s), 9.01 (2H, s), 11.15 (1H, br s).

EXAMPLE 4

3-N-Benzylaminomethyl)-4-methyl-1-[3-(5-(1,2,4-triazol-4-yl)-1H-indol-3-yl)propyl]piperazine. 2.2 Hydrogen Oxalate Step 1: 3-(N-Benzylaminocarbonyl)-4-tert-butyloxycarbonyl-1-[3-(5-(1,2,4-triazol-4-yl)indol-3-yl)propyl]piperazine To a solution of 4-tert-butyloxycarbonyl-1-[3-(5-(1,2,4-triazol-4-yl) -1H-indol-3-yl)propyl]piperazine-3-carboxylic acid ethyl ester contaminated with a small amount of the 2-isomer (524 mg, 1.1 mmol; see Example 3, Step 2) in EtOH (10 mL) was added NaOH (0.54 mL of a 4M aqueous solution, 2.2 mmol). The mixture was heated at 50° C. for 2 h, then cooled to room temperature and evaporated lit vacuo. The residue was dissolved in water (10 mL) and neutralized using 1M hydrochloric acid. The solvent was evaporated and the residue chromatographed on silica gel, eluting with $CH_2Cl_2$:MeOH:AcOH (90:10:1→80:20:2), to afford 4-tert-butyloxycarbonyl -1-[3-(5-(1,2,4-triazol-4-yl)-1H-indol-3-yl)propyl]piperazine-3-carboxylic acid, as a cream-coloured foam, contaminated with a small amount of the 2-isomer.

To a suspension of the acid mixture (0.2 g, 0.44 mmol) in DMF (10 mL) was added benzylamine (58 μL, 0.48 mmol), 1-hydroxybenzotriazole (65 mg, 0.48 mmol), 1-ethyl-3-[3-(dimethylamino)propyl]carbodiimide hydrochloride (93 mg, 0.48 mmol) and triethylamine (0.27 mL, 1.94 mmol). The mixture was stirred at room temperature for 18 h, before more benzylamine (294 μL, 0.24 mmol), 1-ethyl-3-[3-(dimethylamino)propyl]-carbodiimide hydrochloride (47 mg, 0.24 mmol) and triethylamine (341 μL, 0.24 mmol) were added. The mixture was stirred for a further 8 h before more benzylamine (58 μL, 0.48 mmol), 1-hydroxybenzotriazole (65 mg, 0.48 mmol), 1-ethyl-3-[3-(dimethylamino)propyl]carbodiimide hydrochloride (93 mg, 0.48 mmol) and triethylamine (68 μL, 0.48 mmol) were added. The mixture was stirred for a further 16 h then the solvent was removed in vacuo and the residue partitioned between $CH_2Cl_2$ (50 mL) and water (40 mL). The organic layer was separated, washed with $Na_2CO_3$ (sat., 40 mL) and water (50 mL) then dried ($Na_2SO_4$). The solvent was evaporated and the residue chromatographed on silica gel, eluting with $CH_2Cl_2$:MeOH (90:10). The fractions containing the title compound were combined and evaporated in vacuo. The residue was re-chromatographed on silica gel, eluting with $CH_2Cl_2$:MeOH:AcOH (92.5:7.5:1)→(80:20:1). The fractions containing the desired product were combined and evaporated. The residue was partitioned between $CH_2Cl_2$ (50 mL) and $Na_2CO_3$ (10% (w/v), 40 mL). The organic layer was separated, dried ($Na_2SO_4$) and evaporated. The title amide (160 mg, 67%) was isolated as a pale yellow foam. $^1$H nmr (250 MHz, $CDCl_3$) δ 1.44 (9H, s), 1.78–1.95 (2H, m), 1.99–2.12 (2H, m), 2.30–2.50 (2H, m), 2.66–3.16 (4H, m), 3.59–3.64 (1H, m), 4.04 (1H, br s), 4.40–4.58 (2H, m), 4.61–4.80 (1H, br s), 6.50–6.62 (1H, m), 7.10–7.26 (7H, m), 7.45 (1H, d, J=8.6 Hz), 7.64 (1H, s), 8.39 (1H, br s), 8.50 (2H, s). MS (ES$^+$) 544 (M+1).

Step 2: 3-(N-Benzylaminocarbonyl)-4(H)-1-[3-(5-(1,2,4-triazol-4-yl)-1H -indol-3-yl)propyl]piperazine. 1.4 Hydrogen Oxalate To a solution of 3-(N-benzylaminocarbonyl)-4-tert-butyloxycarbonyl -1-[3-(5-(1,2,4-triazol-4-yl)-1H-indol-3-yl)propyl]piperazine (160 mg, 0.29 mmol) in $CH_2Cl_2$ (20 mL) at room temperature, under nitrogen, was added trifluoroacetic acid (2 mL). The mixture was stirred for 6 h then the solvent was evaporated in vacuo. The residue was partitioned between $CH_2Cl_2$ and $Na_2CO_3$ (10% (w/v), 25 mL). The combined organic layers were dried ($Na_2SO_4$) and evaporated. The residue was chromatographed on silica gel, eluting with $CH_2Cl_2$:MeOH:$NH_3$ (90:10:1), to afford the title amine (116 mg, 89%) as a cream-coloured foam. The amine was characterised as its hydrogen oxalate salt. mp 125° C. (dec.). $C_{25}H_{29}N_7O$. 1.4($C_2H_2O_4$). $H_2O$ requires: C, 56.82; H, 5.80; N, 16.69%. Found: C, 56.75; H, 6.08; N, 17.09%. $^1$H nmr (360 MHz, $d_6$-DMSO) δ 1.82–1.92 (2H, m), 2.30–2.42 (2H, m), 2.44–2.52 (2H, m), 2.72–2.80 (2H, m), 2.81–2.90 (1H, m), 2.96–3.06 (1H, m), 3.17–3.25 (2H, m), 3.95–4.00 (1H, m), 4.31 (1H, dd, J=15.4 and 5.8 Hz), 4.40 (1H, dd, J=15.4 and 6.2 Hz), 7.22–7.34 (7H, m), 7.50 (1H, d, J=8.5 Hz), 7.79 (1H, d, J=2.0 Hz), 8.97 (1H, br t), 9.02 (2H, s), 11.14 (1H, br s). MS (ES$^+$) 444 (M+1).

Step 3: 3-(N-Benzylaminocarbonyl)-4-methyl-1-[3-(5-(1,2,4-triazol-4-yl) -1H-indol-3-yl)propyl]piperazine. 1.25 Hydrogen Oxalate To a solution of 3-(N-benzylaminocarbonyl)-4(H)-1-[3-(5-(1,2,4-triazol-4-yl)-1H-indol-3-yl)propyl]piperazine (100 mg, 0.23 mmol) in MeOH (5 mL) at 0° C., under nitrogen, was added acetic acid (38 μL, 0.68 mmol), sodium cyanoborohydride (28 mg, 0.45 mmol) and formaldehyde (21 μL of a 37% (w/v) solution in water, 0.27 mmol). The cooling bath was removed and the mixture stirred at room temperature for 1 h. After this time $K_2CO_3$ (sat., 10 mL) was added to the mixture and after 15 min. the solvents were removed in vacuo. The residue was partitioned between water (20 mL) and $CH_2Cl_2$ (2×25 mL). The combined organic layers were dried ($Na_2SO_4$) and evaporated. The residue was chromatographed on silica gel, eluting with $CH_2Cl_2$:MeOH:$NH_3$ (92.5:7.5:1). The fractions containing the desired product were combined and evaporated. The residue was re-chromatographed on silica gel, eluting with $CH_2Cl_2$:MeOH (95:5→90:10), to afford the title piperazine (92 mg, 89%) as a colourless foam. The piperazine was characterised as its hydrogen oxalate salt. mp. 118° C. (dec.). $C_{26}H_{31}N_7O$. 1.25($C_2H_2O_4$). $H_2O$ requires: C, 58.20; H, 6.08; N, 16.67%. Found: C, 57.90; H, 5.73; N, 17.06%. $^1$H nmr (360 MHz, d6-DMSO) δ 1.87–2.00 (2H, m), 2.34 (3H, s), 2.52–2.80 (7H, m), 3.00–3.11 (2H, m), 3.13–3.26 (2H, m), 4.31 (2H, d, J=5.9 Hz), 7.20–7.35 (7H, m), 7.50 (1H, d, J=8.6 Hz), 7.79 (1H, s), 8.72 (1H, br s), 9.03 (2H, s), 11.14 (1H, br s). MS (ES$^+$) 458 (M+1).

Step 4: 3-(N-Benzylaminomethyl)-4-methyl-1-[3-(5-(1,2,4-triazol-4-yl)-1H -indol-3-yl)propyl]piperazine. 2.2 Hydrogen Oxalate To a solution of 3-(N-benzylaminocarbonyl)-4-methyl-1-[3-(5-(1,2,4-triazol-4-yl)-1H-indol-3-yl)propyl]piperazine (29 mg, 0.06 mmol) in THF (5 mL) at room temperature, under nitrogen, was added borane-THF (1.0 mL of a 1.0M solution in THF, 1.0 mmol). The mixture was heated at reflux for 18 h, then cooled to room temperature. MeOH (2 mL) was added and the solvents evaporated. The residue was dissolved in EtOH (10 mL), and $K_2CO_3$ (17 mg, 0.13 mmol) was added. The mixture was heated at 75° C. for 20 h, before the solvent was evaporated. The residue was chromatographed on silica gel, eluting with $CH_2Cl_2$:MeOH:$NH_3$ (95:5:1), to afford the amine (12 mg, 45%) as a gum. The title compound was characterised as its hydrogen oxalate salt. $^1$H nmr (360 MHz, d$_6$-DMSO) δ 1.80–1.96 (2H, m), 2.31 (3H, s), 2.37–2.62 (4H, m), 2.66–2.79 (3H, m), 2.80–3.06 (6H, m), 3.98 (1H, d, J=13.4 Hz), 4.03 (1H, d, J=13.4 Hz), 7.28–7.50 (8H, m), 7.78 (1H, s), 9.02 (2H, s), 11.12 (1H, br s). MS (ES$^+$) 444 (M+1).

EXAMPLE 5

3-(N-Benzyl-N-methylaminocarbonyl)-4-methyl-1-[3-(5-(1,2,4-triazol-4-yl) -1H-indol-3-yl)propyl] piperazine. 1.3 Hydrogen Oxalate Step 1: 3-(N-Benzyl-N-methylaminocarbonyl)-4-tert-butyloxyyarbonyl 1-[3-(5-(1,2,4-triazol-4-yl)-1H-indol-3-yl)propyl]piperazine In the same way as that described in Example 4, Step 1, using 4-tert-butyloxycarbonyl-1-[3-(5-(1,2,4-triazol-4-yl)-1H-indol-3-yl)propyl]piperazine-3-carboxylic acid (200 mg, 0.44 mmol), N-benzylmethylamine (163 μL, 0.48 mmol), 1-hydroxybenzotriazole (65 mg, 0.48 mmol), 1-ethyl-3-[3-(dimethylamino)propyl]carbodiimide hydrochloride (93 mg, 0.48 mmol), triethylamine (67 μL, 0.48 mmol) and DMF (5 mL). The residue was chromatographed on silica gel, eluting with $CH_2Cl_2$:MeOH:AcOH (90:10:1→80:20:0), and the fractions containing the title compound were combined and evaporated. The residue was partitioned between $CH_2Cl_2$ (25 mL) and $Na_2CO_3$ (10% (w/v), 20 mL) and the organic phase separated and dried. The solvent was evaporated in vacuo to afford the title compound (205 mg, 84%) as a pale yellow foam.

$^1$H nmr (360 MHz, CDCl$_3$) δ 1.44 (9H, s), 1.81–1.97 (2H, m), 2.00–2.12 (1H, m), 2.20–2.32 (3H, m), 2.71–2.82 (3H, m), 2.93 (3H, br s), 3.00–3.16 (1H 3.70–3.85 (2H, m), 4.24–5.19 (3H, m), 7.13–7.20 (7H, m), 7.47 (1H, d, J=8.6 Hz), 7.56 (1H, s), 8.41 (1H, br s), 8.46 (2H, s). MS (ES$^+$) 558 (M+1).

Step 2: 3-(N-Benzyl-N-methylaminocarbonyl)-4(H)-1-[3-(5-(1,2,4-triazol-4-yl)-1H-indol-3-yl)propyl]piperazine. 1.1 Hydrogen Oxalate In the same way as that described in Example 4, Step 2, using 3-(N-benzyl-N-methylaminocarbonyl) -4-tert-butyloxycarbonyl-1-[3-(5-(1,2,4-triazol-4-yl)-1H-indol-3-yl)propyl]piperazine (205 mg, 0.37 mmol), trifluoroacetic acid (2 mL) and $CH_2Cl_2$ (20 mL). The amine (168 mg, 100%) was isolated as a pale yellow foam. The piperazine was characterized as its hydrogen oxalate salt. mp. 128° C. (dec.). $C_{26}H_{31}N_7O.1.1(C_2H_2O_4)$. $H_2O$ requires: C, 58.94; H, 6.17; N, 17.06%. Found: C, 58.84; H, 6.13; N, 17.43%. $^1$H nmr (360 MHz, d$_6$-DMSO) δ 1.62–1.95 (2H, m), 2.10–2.48 (2H, m), 2.56–2.68 (4H, m), 2.86–3.08 (5H, m), 3.13–3.26 (2H, m), 4.37–4.49 (2H, m), 4.60–4.69 (1H, m), 7.22–7.34 (7H, m), 7.48 (1H, d, J=8.6 Hz), 7.72 (1H, s), 9.01 (2H, s), 11.12 (1H, br s). MS (ES$^+$) 458 (M+1).

Step 3: 3-(N-Benzyl-N-methylaminocarbonyl)-4-methyl-1-[3-(5-(1,2,4-triazol-4-yl)-1H-indol-3-yl)propyl]piperazine. 1.3 Hydrogen Oxalate In the same way as that described in Example 4, Step 3, using 3-(N-benzyl-N-methylaminocarbonyl) -4(H)-1-[3-(5-(1,2,4-triazol-4-yl)-1H-indol -3-yl)propyl]piperazine (108 mg, 0.24 mmol), sodium cyanoborohydride (30 mg, 0.47 mmol), acetic acid (41 μL, 0.71 mmol), formaldehyde (224 μL of a 38% (w/v) solution in water, 0.28 mmol) and MeOH (5 mL). The residue was chromatographed on silica gel, eluting with $CH_2Cl_2$:MeOH:$NH_3$ (90:10:1), to afford the title amide (88 mg, 79%) as a colourless foam. The amide was characterised as the hydrogen oxalate salt. mp. 111° C. (dec.). $C_{27}H_{33}N_7O.1.3$ $(C_2H_2O_4)$. $H_2O$ requires: C, 58.60; H, 6.25; N, 16.16%. Found: C, 58.57; H, 6.37; N, 16.49%. $^1$H nmr (360 MHz, d$_6$-DMSO) δ 1.77–2.00 (2H, m), 2.39 (3H, br s), 2.59–3.20 (13H, m), 4.40–4.80 (3H, m), 7.21–7.36 (7H, m), 7.48 (1H, d, J=8.6 Hz), 7.72 (1H, s), 9.01 (2H, s), 11.15 (1H, br s). MS (ES$^+$) 472 (M+1).

EXAMPLE 6

4-Benzyl-3-(N,N-dimethylaminomethyl)-1-[3-(5-(1,2,4-triazol-4-yl)-1H -indol-3-yl)propyl]piperazine. Oxalate Step 1: 1-Benzyl-2-(N,N-dimethylcarboxamido)piperazine 1-Benzyl-2-(ethoxycarbonyl)piperazine (7 g, prepared according to *Synthesis,* 1991, 318) was dissolved in $CH_2Cl_2$ and di-tert-butyl dicarbonate (12.32 g) added. The reaction was stirred for 1 h, the solvent removed in vacuo and replaced with MeOH (150 mL). LiOH (500 mg) was added and the reaction heated to reflux for 2 h. The MeOH was then evaporated and the residue acidified with citric acid.

The aqueous layer was extracted with ethyl acetate (100 mL), the organic layer dried over MgSO₄, and the solvent removed in vacuo.

The 1-benzyl-4-tert-butyloxycarbonylpiperazine-2-carboxylic acid (2.64 g, 8.25 mmol) prepared according to the preceding paragraph was suspended in DMF (120 mL) and 1-(3-(dimethylamino)propyl)-3-ethylcarbodiimide hydrochloride (1.74 g, 9.08 mmol), 1-hydroxybenzotriazole (1.12 g, 8.25 mmol) and triethylamine (1.15 mL, 8.25 mmol) added. The reaction was stirred under N₂ for 2 h and dimethylamine (5.6M solution in EtOH, 4 mL) added. The clear solution was stirred under N₂ for 72 h. The solvent was removed in vacuo and the residue azeotroped with xylenes. The residue was partitioned between ethyl acetate (200 mL) and H₂O (120 mL), dried (MgSO₄) and the solvent removed in vacuo. The residue was chromatographed on silica eluting with 2–4% MeOH/CH₂Cl₂ to obtain an oil that was treated with HCl/MeOH for 1 h. The excess acid was removed in vacuo. The residue was basified to pH 13 with K₂CO₃ and extracted with ethyl acetate. The organic layer was collected, dried (MgSO₄) and the solvent removed in vacuo to obtain the title compound as a colourless oil (1.5 g). $^1$H nmr (250 MHz, CDCl₃) δ 2.10–2.4 (2H, m), 2.21 (6H, s), 2.50–2.88 (4H, m), 3.0 (1H, dd, J=1.4 Hz), 3.20 (1H, d, J=5 Hz), 4.20 (1H, d, J=5 Hz), 7.22–7.35 (5H, m).

Step 2: 1-Benzyl-2-(N,N-dimethylaminomethyl)piperazine

To a solution of 1-benzyl-2-(N,N-dimethylcarboxamido) piperazine (2.5 g, 3.06 mmol) in THF (30 mL) was added lithium aluminium hydride (4 mL, 1.0M solution in THF) dropwise at 0° C. The reaction was then heated to reflux for 16 h, cooled to 0° C. and quenched by the addition of ice-water (5 mL), NaOH (4N, 5 mL) and water (15 mL). The resulting white precipitate was stirred for 15 min, and filtered through celite and washed with ether. The filtrate was evaporated in vacuo, the residue azeotroped with toluene and the residue chromatographed on alumina, eluting with 1–5% MeOH:1% NH₃:CH₂Cl₂, to obtain the title compound as a pale yellow oil, 0.520 g. $^1$H nmr (250 MHz, CDCl₃) δ 2.04 (2H, m), 2.26 (1H, m), 2.89–3.15 (5H, m), 2.97 (6H, s), 3.40 (2H, m), 3.80 (1H, d), 7.29 (5H, m). MS (m/z) 234 (M+1).

Step 3: 4-Benzyl-3-(N,N-dimethylaminomethyl)-1-[3-(5-(1,2,4-triazol-4-yl) -1H-indol-3-yl)propyl]piperazine. Oxalate To a solution of 3-[5-(1,2,4-triazol-4-yl)-1H-indol-3-yl] propan-1-ol (0.490 g, 2.02 mmol) in THF (100 mL) was added triethylamine (0.62 ml), 6.0 mmol) followed by methanesulphonyl chloride (0.35 mL, 3.03 mmol) and the mixture stirred at 25° C. for 1.5 h. The reaction mixture was filtered and the solvent evaporated. The residue was dissolved in DMF (50 mL) and potassium carbonate (0.35 g) added followed by a solution of 1-benzyl-2-(N,N-dimethylaminomethyl)piperazine (step 2) (0.52 g, 2.22 mmol) in DMF (20 mL). The reaction was heated at 85° C. under N₂ for 4 days. The solvent was then removed in vacuo and the residue taken up in ethyl acetate (50 mL) and washed with H₂O (3×20 mL). The organic layer was dried (MgSO₄) and evaporated. The residue was chromatographed on silica eluting with CH₂Cl₂→6% MeOH-1% NH₃—CH₂Cl₂ to obtain a pale yellow oil that was treated with a solution of oxalic acid in ethyl acetate to obtain a white solid that was filtered and dried to obtain 4-benzyl-3-(N,N-dimethylaminomethyl)-1-[3-(5-(1,2,4-triazol-4-yl) -1H-indol-3-yl)propyl]piperazine oxalate, 105 mg. $^1$H nmr (free base, 250 MHz, CDCl₃) δ 1.92 (2H, m), 2.05–2.9 (13H, m), 2.21 (6H, s), 3.22 (1H, d), 4.20 (1H, d), 7.12 (2H, m), 7.23–7.31 (5H, m), 7.46 (1H, d, J=4 Hz), 7.55 (1H, d, J=1 Hz), 8.38 (1H, br s), 8.46 (2H, s). MS (m/z) 458 (M+1).

We claim:
1. A compound of formula I, or a pharmaceutically acceptable salt thereof:

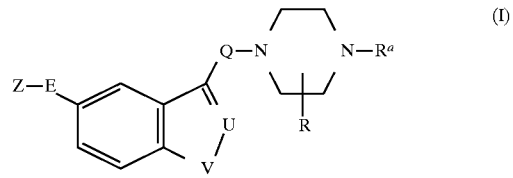

wherein

Z represents an optionally substituted five-membered heteroaromatic ring selected from furan, thiophene, pyrrole, oxazole, thiazole, isoxazole, isothiazole, imidazole, pyrazole, oxadiazole, thiadiazole, triazole and tetrazole wherein the optional substituents are methyl, ethyl, benzyl or amino;

E represents a chemical bond or a straight or branched alkylene chain having from 1 to 4 carbon atoms;

Q represents a straight or branched alkylene chain having from 1 to 6 carbon atoms, optionally substituted in any position by a hydroxy group;

U represents C—R²;

V represents N—R³;

R represents a group of formula —W—R¹;

W represents a carbonyl group (C=O), or a straight or branched alkylene chain having from 1 to 4 carbon atoms;

R¹ represents —OR$^x$, —OCOR$^x$, —OCONR$^x$R$^y$, —NR$^x$R$^y$, —NR$^z$COR$^x$ or —NR$^z$CONR$^x$R$^y$;

R$^x$ and R$^y$ independently represent hydrogen, methyl, benzyl, methoxy-benzyl, acetylamino-benzyl, 1-phenylethyl, 2-phenylethyl, 2-hydroxy-1-phenylethyl, 1-(acetylamino-phenyl)ethyl, 2-(acetylaminophenyl)ethyl, 1-hydroxy-3-phenylprop-2-yl, 1-hydroxy-1-phenylprop-2-yl, furylmethyl, thienylmethyl and -pridylmethyl;

R$^a$ and R$^z$ independently represent hydrogen, methyl or benzyl; and

R² and R³ independently represent hydrogen or C₁₋₆ alkyl.

2. A compound as claimed in claim 1 represented by formula II, or a pharmaceutically acceptable salt thereof:

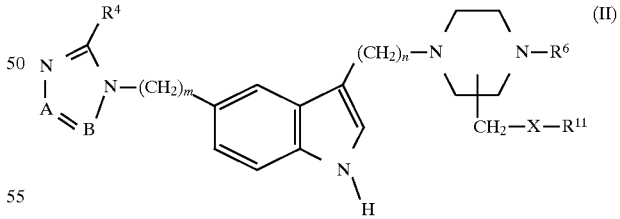

wherein m is zero, 1, 2 or 3;

n is 2,3 or 4;

A represents nitrogen or CH;

B represents nitrogen or C—R⁵;

X represents oxygen or N—R¹²; R⁴ and R⁵ independently represent hydrogen, methyl, ethyl, benzyl or amino;

R⁶ represents methyl or benzyl; and

R¹¹ and R¹² independently represent hydrogen, methyl, acetyl, benzyl, methoxy-benzyl, acetylamino benzyl, 1-phenylethyl, 2-phenylethyl, 2-hydroxy-1-phenylethyl, 1-(acetylamino-phenyl)ethyl, 2-(acetylaminophenyl)ethyl, 1-hydroxy-3-phenylprop-2-yl, 1-hydroxy-1-phenylprop-2-yl, furylmethyl, thienylmethyl and pyridylmethyl.

3. A compound selected from:
4-benzyl-2-hydroxymethyl-1-[3-(5-(1,2,4-triazol-4-yl)-1H-indol-3-yl)propyl]piperazine;
4-benzyl-3-hydroxymethyl-1-[3-(5-(1,2,4-triazol-4-yl)-1H-indol-3-yl)propyl]piperazine;
2-acetamidomethyl-4-benzyl-1-[3-(5-(1,2,4-triazol-4-yl)-1H-indol-3-yl)propyl]piperazine;
and salts thereof.

4. A compound selected from:
3-(N-benzylaminomethyl)-4-methyl-1-[3-(5-(1,2,4-triazol-4-yl)-1H-indol-3-yl)propyl]piperazine;
3-(N-benzyl-N-methylaminocarbonyl)-4-methyl-1-[3-(5-(1,2,4-triazol-4-yl) -1H-indol-3-yl)propyl]piperazine;
4-benzyl-3-(N,N-dimethylaminomethyl)-1-[3-(5-(1,2,4-triazol-4-yl)-1H -indol-3-yl)propyl]piperazine;
and salts thereof.

5. A pharmaceutical composition comprising a compound as claimed in claim 1 in association with a pharmaceutically acceptable carrier.

6. A method for the treatment and/or prevention of migraine, cluster headache, chronic aroxysmal hemicrania, headache associated with vascular disorders, tension headache and pediatric migraine which method comprises administering to a patient in need of such treatment an effective amount of a compound as claimed in any one of claims 1 to 4.

7. A process for the preparation of a compound as claimed in claim 1 which comprises:

(A) attachment of the $R^a$ moiety to a compound of formula III:

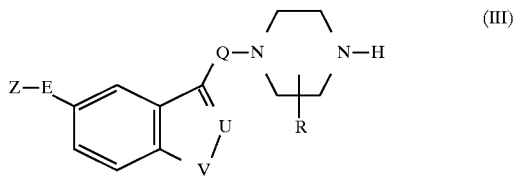

(III)

by N-alkylation or reductive alkylation wherein Z, E, Q, U, V and R are as defined in claim 1; or (B) reacting a compound of formula IV:

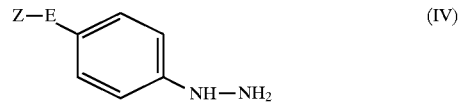

(IV)

wherein Z and E are as defined in claim 1; with a compound of formula IX, or a carbonyl-protected form thereof:

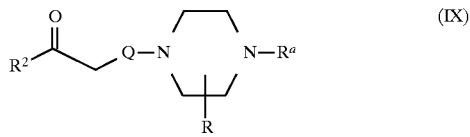

(IX)

wherein Q, R, $R^a$ and $R^2$ are as defined in claim 1; followed optionally by N-alkylation to introduce the moiety $R^3$; or (C) reacting a compound of formula XI:

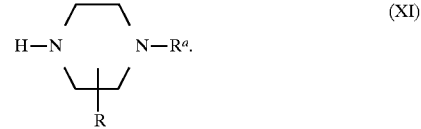

(XI)

wherein R and $R^a$ are as defined in claim 1; with a compound of formula XII:

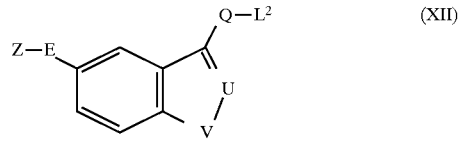

(XII)

wherein Z, E, Q, U and V are as defined in claim 1, and $L^2$ represents a suitable leaving group.

* * * * *